United States Patent
Matsumoto et al.

(10) Patent No.: US 9,447,362 B2
(45) Date of Patent: Sep. 20, 2016

(54) NITRILE COMPOUND

(71) Applicant: Kao Corporation, Tokyo (JP)

(72) Inventors: Tomotaka Matsumoto, Tokyo (JP); Takashi Aoki, Wakayama (JP); Takahiro Hirose, Chiba (JP); Shoichi Tahara, Chiba (JP); Herwick Tan, Zeeland (NL); Natacha Jerome, Barcelona (ES)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 14/655,573

(22) PCT Filed: Dec. 9, 2013

(86) PCT No.: PCT/JP2013/082990
§ 371 (c)(1),
(2) Date: Jun. 25, 2015

(87) PCT Pub. No.: WO2014/103685
PCT Pub. Date: Jul. 3, 2014

(65) Prior Publication Data
US 2015/0353480 A1    Dec. 10, 2015

(30) Foreign Application Priority Data
Dec. 26, 2012    (JP) .................................. 2012-283537

(51) Int. Cl.
| A61Q 19/00 | (2006.01) |
| A61K 8/40  | (2006.01) |
| C07C 253/30 | (2006.01) |
| C07C 255/31 | (2006.01) |
| C11B 9/00  | (2006.01) |
| C11D 3/50  | (2006.01) |

(52) U.S. Cl.
CPC ............... *C11B 9/0034* (2013.01); *A61K 8/40* (2013.01); *A61Q 19/00* (2013.01); *C07C 253/30* (2013.01); *C07C 255/31* (2013.01); *C11D 3/50* (2013.01); *A61K 2800/10* (2013.01); *C07C 2101/14* (2013.01)

(58) Field of Classification Search
None
See application file for complete search history.

(56) References Cited

U.S. PATENT DOCUMENTS

| 3,168,550 A | 2/1965 | Blumenthal |
| 4,193,934 A | 3/1980 | Bauer et al. |
| 5,011,970 A | 4/1991 | Lenselink |
| 2002/0086901 A1 | 7/2002 | Bajgrowicz et al. |
| 2010/0137178 A1 | 6/2010 | Smets et al. |

FOREIGN PATENT DOCUMENTS

| CN | 102 300 550 | 12/2011 |
| DE | 23 48 359 A1 | 4/1975 |
| EP | 0 797 569 A1 | 10/1997 |
| JP | S49-81342 A | 8/1974 |
| JP | H11-501614 A | 2/1999 |
| JP | 2012-510561 A | 5/2012 |
| WO | WO 96/18604 A1 | 6/1996 |

OTHER PUBLICATIONS

International Search Report issued Jan. 7, 2014, in PCT/JP2013/082990, filed Dec. 9, 2013.
Motoichi Indo, "Cuminyl nitrile & Peonile", Synthetic perfume, Chemistry and product knowledge, 2005, pp. 701-702 (with partial English translation).
Libor Cerveny, et al., "Fragrant Esters of 3-Cyclohexyl-1-propanol and 3-Cyclohexyl-1-butanol", Perfumer & Flavorist, Mar./Apr. 1991, vol. 16, pp. 37-38.
Extended European Search Report mailed Jul. 25, 2016 in European Patent Application No. 13869174.6.
Sell, C.S., et al., "The Influence of Methyl Group Substitution on the Odour of Allphatic Nitriles", Perfumer & Flavorist, Allured Publishing Corp. Vol. 7, Dec. 1982/Jan. 1983, pp. 14-16.
Yadav, Vasanti G., "Perfumery Nitriles and Acetals: Part II Synthesis and Characteristics of Nitriles", University of Bombay, Pafai Journal, Apr.-Jun. 1994, pp. 29-42.

*Primary Examiner* — Alicia L Otton
(74) *Attorney, Agent, or Firm* — Oblon, McClelland, Maier & Neustadt, L.L.P

(57) ABSTRACT

Provided are a compound and a fragrance composition containing the same, wherein the compound has a spicy tone that is useful as a fragrance, particularly a cumin-like odor, it is stable in an aqueous vehicle, and it emphasizes spicy-, green-, floral-, woody-, and citrus-like various odors by being blended with other fragrances, which allows oil-, chemical-, and metallic-like undesirable odors to be suppressed. A nitrile compound represented by Formula (I-3), Formula (I-2), or Formula (I-1).

[Chemical Formula 45]

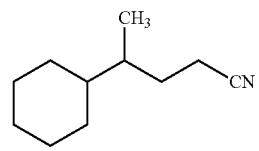

(I-3)

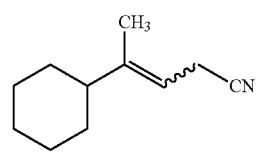

(I-2)

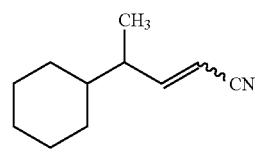

(I-1)

19 Claims, No Drawings

NITRILE COMPOUND

CROSS REFERENCE TO RELATED APPLICATION

This application is a 371 of PCT/JP2013/082990, filed on Dec. 9, 2013, and claims priority to Japanese Patent Application 2012-283537, filed on Dec. 26, 2012.

TECHNICAL FIELD

The present invention relates to a new nitrile compound and a fragrance composition containing the same.

BACKGROUND ART

Fragrance is an important element that creates, for example, preference, a sense of luxury, a sense of ease, and expectations for the effect for products and the like. Furthermore, a distinctive fragrance provides a product differentiation effect and the capacity for attracting customers. On the other hand, in order to control, for example, a long-lasting property and balance of fragrance, generally, a fragrance is imparted to a product using a fragrance composition in which a plurality of fragrance materials are mixed together. It is required for the fragrance materials composing the fragrance composition to be highly harmonious with other fragrance materials.

Cuminyl nitrile, which is a p-isopropylbenzonitrile having a cumin odor, is known as a fragrance material having a cyclic structure and a nitrile structure, while, for example, Peonile (Givaudan), which is 2-cyclohexylidene-2-phenylacetonitrile having grapefruit-, geranium-, and rose floral-like odors, is known as a fragrance material having a cyclohexane ring and a nitrile structure. (Non-Patent Document 1).

In addition, Patent Document 1 describes that 3-cyclohexyl-2,2-dimethylpropanenitrile has intense mint-, marine-, and spicy-like odors, while Patent Document 2 describes that β-(2,4-dimethylcyclohexyl)propionitrile has a spicy caraway fragrance and the unsaturated compound thereof has a herbal-spicy and green fragrance. Furthermore, Patent Document 3 describes that 5-cyclohexyl-3-methylpentanenitrile has wax-, fruit-, cinnamon-, formic acid-, and lemon-like odors.

Very roughly speaking, fragrance materials have similar fragrance notes when they have similar structures to each other, but there are many exceptions. Particularly, when a plurality of substituents are combined to change the fragrance note, it is difficult to predict how the fragrance note will change and it also is difficult to predict the harmonicity with other fragrance materials.

PRIOR ART DOCUMENTS

Non-Patent Document

[Non-Patent Document 1] "Gosei Koryo, Kagaku to Shohin Chishiki" (Synthetic Perfumes, Chemistry and Commodity Knowledge), authored by Genichi Indo, Enlarged and Revised Edition, 2005, pp. 701 to 702

Patent Documents

[Patent Document 1] JP 2012-510561A
[Patent Document 2] JP H11(1999)-501614A
[Patent Document 3] German Patent DE2348359

DISCLOSURE OF INVENTION

Problem to be Solved by the Invention

The present invention is intended to provide a compound and a fragrance composition containing the same, wherein the compound has a spicy tone, particularly a cumin-like odor, is stable in an aqueous vehicle, and emphasizes spicy-, green-, floral-, woody-, and citrus-like various odors by being blended with other fragrances, which allows oil-, chemical-, and metallic-like undesirable odors to be suppressed.

Means for Solving Problem

The present inventors found that a nitrile compound represented by Formula (I-3), Formula (I-2), or Formula (I-1) has a spicy tone, particularly a cumin-like odor, that is useful as a fragrance, it is stable in an aqueous vehicle, and it emphasizes spicy-, green-, floral-, woody-, and citrus-like various odors by being blended with other fragrances, which allows oil-, chemical-, and metallic-like undesirable odors to be suppressed. Thus, the present invention was completed.

That is, the present invention is a nitrile compound represented by Formula (I-3), Formula (I-2), or Formula (I-1).

[Chemical Formula 1]

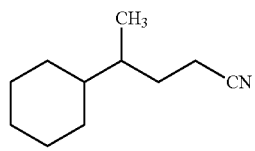
(I-3)

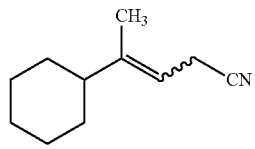
(I-2)

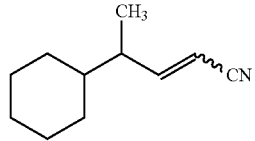
(I-1)

Furthermore, the present invention is a fragrance composition containing a nitrile compound represented by Formula (I-3), Formula (I-2), or Formula (I-1).

Effects of the Invention

The nitrile compound of the present invention has a spicy tone, particularly a cumin-like odor, that is useful as a fragrance, it is stable in an aqueous vehicle, and it emphasizes spicy-, green-, floral-, woody-, and citrus-like various odors by being blended with other fragrances, which allows oil-, chemical-, and metallic-like undesirable odors to be suppressed.

DESCRIPTION OF THE INVENTION

Nitrile Compound

The nitrile compound of the present invention has a structure represented by Formula (I-3), Formula (I-2), or Formula (I-1).

[Chemical Formula 2]

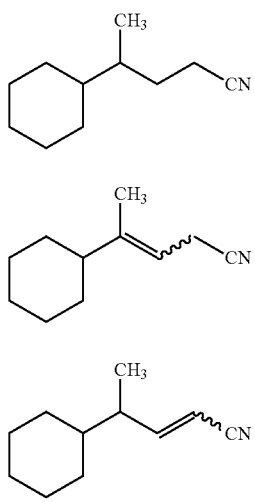

In Formula (I-1) and Formula (I-2), the bond represented by a wavy line indicates a cis form, a trans form, or a mixture of a cis form and a trans form.

Especially, in terms of having a spicy tone, particularly a cumin-like good odor, the nitrile compounds represented by Formula (I-2) and Formula (I-3) below are preferable. In Formula (I-2), the bond represented by a wavy line indicates a cis form, a trans form, or a mixture of a cis form and a trans form.

[Chemical Formula 3]

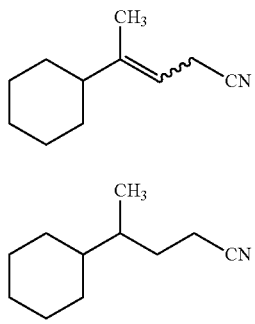

The nitrile compound represented by Formula (I-3) below is more preferable in terms of emphasizing spicy-, green-, floral-, woody-, and citrus-like various odors by being blended with other fragrances, which allows oil-, chemical-, and metallic-like undesirable odors to be suppressed.

[Chemical Formula 4]

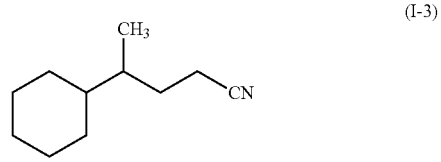

[Method of Producing Nitrile Compound]

The nitrile compound represented by 4-cyclohexyl-2-pentenenitrile (I-1), 4-cyclohexyl-3-pentenenitrile (I-2), or 4-cyclohexylpentanenitrile (I-3) of the present invention can be synthesized utilizing a common organic chemical reaction and the method of producing it is not limited. At least one nitrile compound selected from the group consisting of 4-cyclohexyl-2-pentenenitrile 4-cyclohexyl-3-pentenenitrile (I-2), and 4-cyclohexylpentanenitrile (I-3) may be hereinafter referred to as a "nitrile compound (I)." A suitable method of producing the nitrile compound (I) of the present invention is preferably, for example, a method in which 2-cyclohexylpropanal represented by Formula (II) below (may be hereinafter referred to as "2-cyclohexylpropanal (II)") is subjected to unsaturated nitrilation and thereby 4-cyclohexyl-2-pentenenitrile represented by Formula (I-1) (may be hereinafter referred to as "4-cyclohexyl-2-pentenenitrile (I-1)") and/or 4-cyclohexyl-3-pentenenitrile represented by Formula (I-2) (may be hereinafter referred to as "4-cyclohexyl-3-pentenenitrile (I-2)") are/is obtained (see Scheme 1). The 4-cyclohexyl-2-pentenenitrile (I-1) and/or the 4-cyclohexyl-3-pentenenitrile (I-2) are/is further hydrogenated and thereby 4-cyclohexylpentanenitrile represented by Formula (I-3) (may be hereinafter referred to as "4-cyclohexylpentanenitrile (I-3)") can be obtained (see Scheme 1). In the scheme, the bond represented by a wavy line in Formula (I-1) and Formula (I-2) indicates a cis form, a trans form, or a mixture of a cis form and a trans form.

Scheme 1

[Chemical Formula 5]

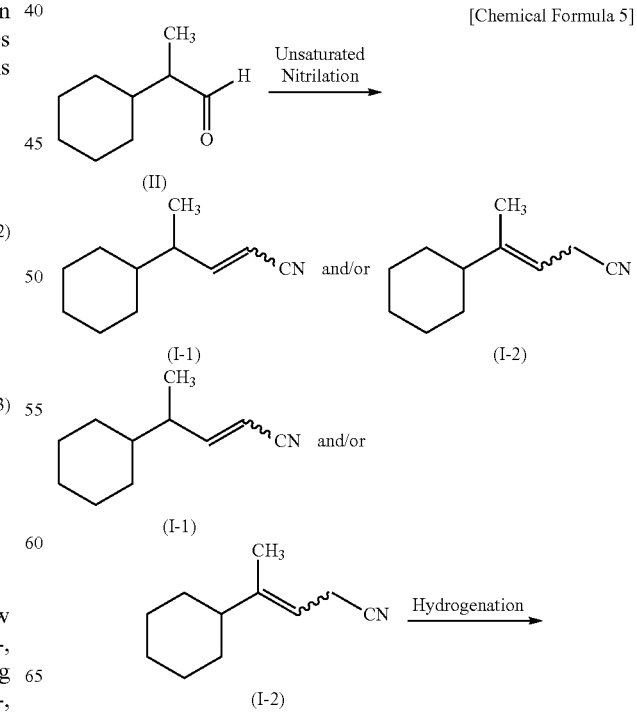

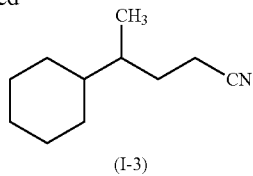

(I-3)

Furthermore, in a suitable method of producing the 4-cyclohexylpentanenitrile (I-3) of the present invention, for example, 2-cyano-4-cyclohexyl pentanoate represented by Formula (VIII) (may be hereinafter referred to as "2-cyano-4-cyclohexyl pentanoate (VIII)") is subjected to dealkoxycarbonylation and thereby the 4-cyclohexylpentanenitrile (I-3) can be obtained (see Scheme 2).

The 2-cyano-4-cyclohexyl pentanoate (VIII) can be produced as follows. For example, the 2-cyclohexylpropanal (II) is condensed with a compound of Formula (VI) (Knoevenagel condensation) and thereby 2-cyano-4-cyclohexylpenta-2-enoate represented by Formula (VII) (may be hereinafter referred to as "2-cyano-4-cyclohexylpenta-2-enoate (VII)") is obtained. Then, the 2-cyano-4-cyclohexylpenta-2-enoate (VII) is further hydrogenated and thereby 2-cyano-4-cyclohexyl pentanoate (VIII) can be obtained (see Scheme 2). In Scheme 2, the bond represented by a wavy line in Formula (VII) indicates a cis form, a trans form, or a mixture of a cis form and a trans form.

In the formulae, R indicates an alkyl group having 1 to 8 carbon atoms, an alkenyl group having 2 to 8 carbon atoms, or an alkyl group having 1 to 8 carbon atoms substituted with alkoxy having 1 to 8 carbon atoms.

The 2-cyclohexylpropanal (II) can be obtained by using, for instance, 2-phenylpropanol as a raw material, carrying out nuclear hydrogenation of the phenyl group, and then oxidizing the alcohol. Examples of commercially available products of the 2-cyclohexylpropanal (II) include Pollenal II (Trade Name) manufactured by Kao Corporation. In the unsaturated nitrilation reaction, acetal of the 2-cyclohexylpropanal (II) also can be used instead of the 2-cyclohexylpropanal (II).

Method of Producing 4-Cyclohexyl-2-Pentenenitrile (I-1)

In terms of the reaction yield and selectivity, the method of producing the 4-cyclohexyl-2-pentenenitrile (I-1) of the present invention is preferably a method including a step of condensing the 2-cyclohexylpropanal (II) and a cyanomethyl phosphonic acid derivative (III), more preferably a method including a step of condensing the 2-cyclohexylpropanal (II) and a cyanomethyl phosphonic acid derivative (III) in the presence of an activator. In Formula (I-1), the bond represented by a wavy line indicates a cis form, a trans form, or a mixture of a cis form and a trans form.

Scheme 2

[Chemical Formula 6]

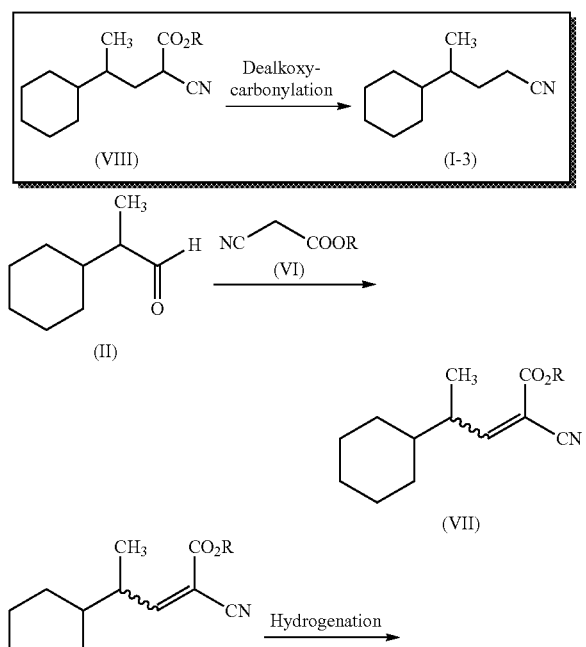

[Chemical Formula 7]

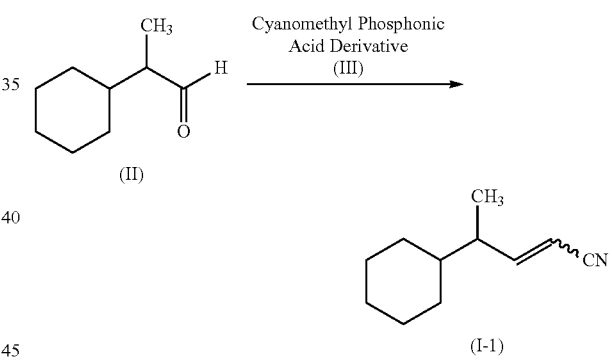

Specifically, the 4-cyclohexyl-2-pentenenitrile (I-1) is obtained preferably by a Horner-Wadsworth-Emmons reaction in which diester of cyanomethylphosphonic acid represented by Formula (III-A) below is used as the cyanomethyl phosphonic acid derivative (III) or by a Wittig reaction in which cyanomethyl phosphonium salt represented by Formula (III-B) below is used as the cyanomethyl phosphonic acid derivative (III). Preferably, it is obtained by the Horner-Wadsworth-Emmons reaction, in which the diester of cyanomethylphosphonic acid (III-A) is used, from the viewpoints that the reaction proceeds under a mild condition and it is excellent in reactivity.

[Chemical Formula 8]

(III-A)

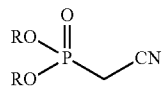

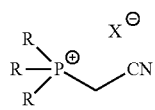

(III-B)

[In the formulae, R indicates an alkyl group or phenyl group having 1 to 6 carbon atoms and X indicates a halogen atom (an iodine atom, a bromine atom, a chlorine atom, or a fluorine atom).]

The ester portions (the above-mentioned formula R) of the diester of cyanomethylphosphonic acid (III-A) used in the Horner-Wadsworth-Emmons reaction each are preferably a linear or branched alkyl group or phenyl group having 1 to 6 carbon atoms, more preferably a linear or branched alkyl group having 1 to 3 carbon atoms, and in terms of the cost and handling, further preferably a methyl group or an ethyl group.

The amount of the diester of cyanomethylphosphonic acid (III-A) to be used with respect to the 2-cyclohexylpropanal (II) is preferably 0.5 to 2 times by mole, more preferably 0.8 to 1.2 times by mole, and in terms of improving the yield, further preferably 1.00 to 1.10 times by mole, with respect to the 2-cyclohexylpropanal (II).

The activator is used to cause enolization or deprotonation on the carbon atom adjacent to the nitrile group of the diester of cyanomethylphosphonic acid (III-A) to activate the reaction. Examples of the activator include alkoxides of alkali metals or alkaline earth metals, alkali metal hydrides, alkyllithiums, alkali metal amides, and a Grignard reagent. In terms of the yield, cost, reaction activity, and handling, the activator is preferably an alkoxide of an alkali metal or alkaline earth metal, more preferably an alkoxide of an alkali metal, and further preferably an alkoxide of an alkali metal of an alcohol having 1 to 6 carbon atoms.

The alkoxide of an alkali metal of an alcohol having 1 to 6 carbon atoms is preferably sodium methoxide, sodium ethoxide, potassium methoxide, potassium ethoxide, sodium propoxide, potassium propoxide, sodium isopropoxide, potassium isopropoxide, sodium butoxide, potassium butoxide, sodium tert-butoxide, or potassium tert-butoxide, more preferably sodium methoxide, sodium ethoxide, potassium tert-butoxide, or potassium tert-butoxide, and in terms of handling, further preferably potassium tert-butoxide.

The amount of the activator to be used is, with respect to the 2-cyclohexylpropanal, preferably 0.001 times by mole to 10 times by mole in terms of the reaction activity, more preferably 0.005 times by mole to 5 times by mole in terms of the yield, and further preferably 0.01 times by mole to 2 times by mole in terms of the yield and cost.

In terms of suppressing the decomposition of a substrate and improving the selectivity and yield, the reaction temperature is preferably −80 to 120° C., more preferably −20 to 80° C., and further preferably 0 to 50° C.

This reaction may be carried out in the absence of a solvent, but in terms of the yield, selectivity, and handling, it is preferable to use a solvent. Examples of the solvent include hydrocarbons, halogenated solvents, ethers, ketones, esters, and alcohols. Among these, hydrocarbons, ethers, and alcohols are preferable since they are inactive to the reaction, and hydrocarbons are preferable. Examples of hydrocarbons include toluene, xylene, benzene, and hexane, and toluene and xylene are preferable.

The reaction pressure can be under atmospheric pressure. However, in order to obtain sufficient reaction temperature and reactivity, the reaction may be carried out under pressure, for example, at 0.1 to 20 MPa.

In terms of improving the quality as a fragrance material, it is preferable that the 4-cyclohexyl-2-pentenenitrile (I-1) obtained herein be purified by, for example, extraction, distillation, or silica gel column chromatography.

Method of Producing 4-Cyclohexyl-3-pentenenitrile (I-2)

In terms of the yield and selectivity, the method of producing the 4-cyclohexyl-3-pentenenitrile (I-2) of the present invention is preferably a method including a step of condensing the 2-cyclohexylpropanal (II) and cyanoacetic acid (IV) (Knoevenagel condensation) and a step of decarboxylating the condensate thus obtained, more preferably a method including a step of condensing the 2-cyclohexylpropanal (II) and cyanoacetic acid (IV) in the presence of an activator and a step of decarboxylating the condensate thus obtained. In Formula (I-2), the bond represented by a wavy line indicates a cis form, a trans form, or a mixture of a cis form and a trans form.

[Chemical Formula 9]

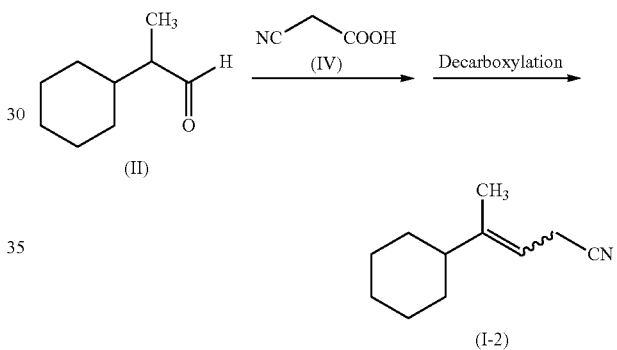

Examples of the activator that is used in the condensation reaction include organic amines, amino acids, and ammonium salts. The activator is preferably an ammonium salt in terms of the yield and reaction activity. Particularly, ammonium acetate is more preferable in terms of handling.

The amount of the activator to be used is, with respect to the 2-cyclohexylpropanal (II), preferably 0.001 times by mole to 10 times by mole, more preferably 0.005 times by mole to 5 times by mole in terms of the yield, and further preferably 0.01 times by mole to 2 times by mole in terms of the yield and cost.

The amount of the cyanoacetic acid (IV) to be used with respect to the 2-cyclohexylpropanal (II) in the condensation reaction is, with respect to the 2-cyclohexylpropanal (II), preferably 0.5 to 2 times by mole, more preferably 0.8 to 1.2 times by mole, and in terms of improving the yield, further preferably 1.01 to 1.10 times by mole.

In the condensation reaction, the reaction temperature is preferably 50 to 300° C. in terms of completing the condensation reaction efficiently and more preferably 70 to 250° C. in terms of increasing the yield.

In the condensation reaction, in terms of improving the reaction efficiency, it is preferable that the reaction be carried out while water produced as a byproduct by the reaction is removed.

The method of removing water is preferably a method using a water scavenger (for example, a molecular sieve) or a method in which azeotropic dehydration is carried out under solvent reflux, with the solvent forming an azeotropic mixture with water. In terms of removing the reaction heat, it is preferably, for example, a method using azeotropic dehydration.

In the method of removing water by azeotropic dehydration, the solvent to be used is preferably a solvent with a boiling point of 50 to 300° C. and in terms of increasing the yield, more preferably a solvent with a boiling point of 70 to 250° C. Specifically, in the method of removing water by azeotropic dehydration, the solvent to be used is preferably a nonpolar hydrocarbon solvent such as benzene, toluene, xylene, cymene, or cyclohexane, and in terms of the safety and easiness of solvent removal, more preferably toluene, xylene, or cyclohexane, further preferably toluene or cyclohexane.

In this production method, the condensation reaction is followed by decarboxylation and thereby 4-cyclohexyl-3-pentenenitrile (I-2) is obtained. The decarboxylation may be carried out after the condensate is isolated or may be carried out using a reaction mixture without isolating the condensate. However, in terms of improving the purity of the product, it is preferable to carry out the decarboxylation after the condensate is isolated. The decarboxylation can be carried out by a known method but a method using heating is preferable.

The reaction temperature for the decarboxylation is preferably 50 to 300° C. in terms of completing the reaction efficiently and suppressing thermal decomposition and polymerization of the condensate and 4-cyclohexyl-3-pentenenitrile (I-2), more preferably 100 to 250° C. in terms of increasing the yield.

For the decarboxylation, a high boiling point solvent may be used, but it is preferable to carry out the decarboxylation without using a solvent in terms of the yield, selectivity, and reaction activity.

With respect to the reaction pressure, the decarboxylation can be carried out under atmospheric pressure. However, in terms of efficiently distilling the 4-cyclohexyl-3-pentenenitrile (I-2) to be produced and suppressing thermal decomposition and polymerization of the product, the decarboxylation is carried out preferably under reduced pressure, more preferably at 0.01 to 100 kPa.

In terms of improving the quality as a fragrance material, it is preferable that the 4-cyclohexyl-3-pentenenitrile (I-2) obtained herein be purified by, for example, extraction, distillation, or silica gel column chromatography.

Method of Producing Mixture of 4-Cyclohexyl-2-Pentenenitrile (I-1) and 4-Cyclohexyl-3-Pentenenitrile (I-2)

The method of producing a mixture of the 4-cyclohexyl-2-pentenenitrile (I-1) and the 4-cyclohexyl-3-pentenenitrile (I-2) according to the present invention is preferably a method including a step of condensing 2-cyclohexylpropanal (II) and acetonitrile (V) (an acetonitrile method) or a method including a step of isomerizing the 4-cyclohexyl-3-pentenenitrile (I-2) obtained by the method described above (an isomerization method), more preferably the isomerization method in terms of the easiness of controlling the selectivity.

[Chemical Formula 10]

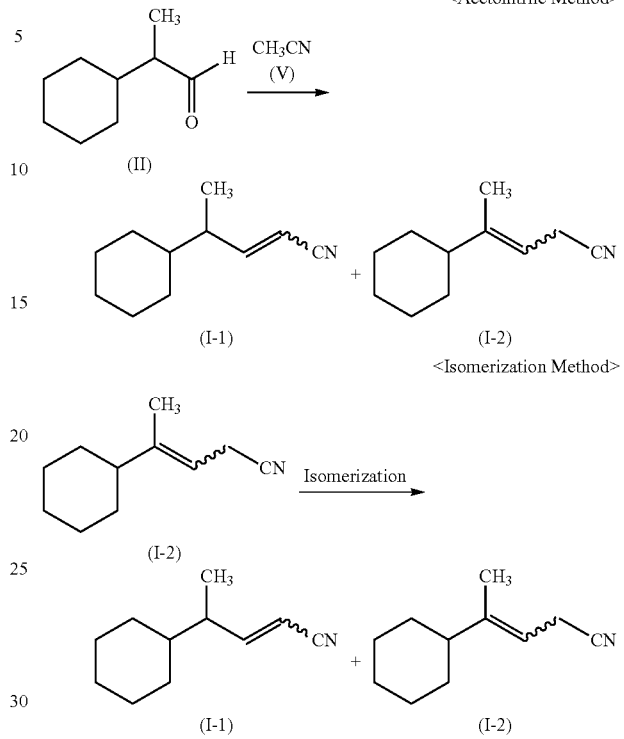

The bond represented by a wavy line in Formula (I-1) and Formula (I-2) indicates a cis form, a trans form, or a mixture of a cis form and a trans form.

<Acetonitrile Method>

The method including a step of condensing 2-cyclohexylpropanal (II) and acetonitrile (V) is preferably a method including a step of condensing 2-cyclohexylpropanal (II) and acetonitrile (V) in the presence of an activator in terms of the yield and selectivity.

[Chemical Formula 11]

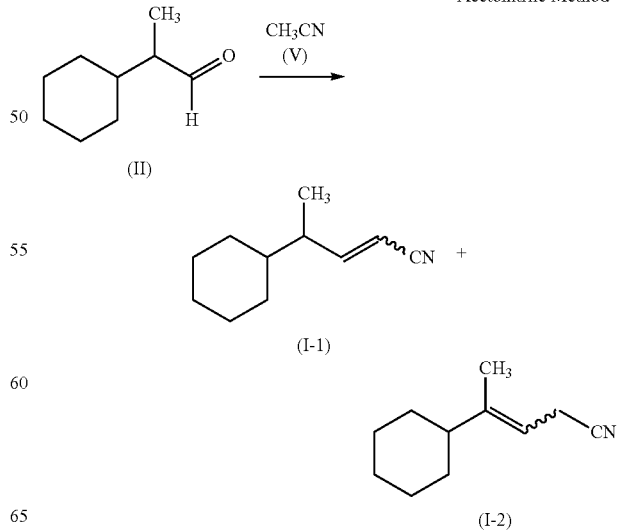

The bond represented by a wavy line in Formula (I-1) and Formula (I-2) indicates a cis form, a trans form, or a mixture of a cis form and a trans form.

Examples of the activator that is used in this method include hydroxides of alkali metals or alkaline earth metals, alkoxides of alkali metals or alkaline earth metals, alkyllithiums, alkali metal amides, ammonium salts, and basic ion exchange resins. Particularly, in terms of the yield, reaction activity, and handling, the activator is preferably a hydroxide of an alkali metal or an alkaline earth metal, more preferably a hydroxide of an alkali metal. The hydroxide of an alkali metal or an alkaline earth metal is preferably lithium hydroxide, sodium hydroxide, potassium hydroxide, or barium hydroxide, and in terms of the reaction activity, more preferably sodium hydroxide or potassium hydroxide, further preferably potassium hydroxide.

In terms of increasing the reaction rate and yield, the reaction temperature is preferably 0 to 150° C., more preferably 50 to 100° C.

In this reaction, a solvent may be used. In terms of increasing the solubility of the activator and improving the reaction activity, hydrocarbons, alcohols, phase transfer catalysts such as crown ether, and dimethyl sulfoxide are preferable as the solvent. However, it is more preferable to use acetonitrile not only as a reaction component but also as a solvent, and it is preferable to use acetonitrile in an amount of at least 0.01 times by mole with respect to the 2-cyclohexylpropanal (II).

<Isomerization Method>

In terms of the yield and selectivity, the method including a step of isomerizing the 4-cyclohexyl-3-pentenenitrile (I-2) obtained by the method described above is preferably a method including a step of isomerizing the 4-cyclohexyl-3-pentenenitrile (I-2) obtained by the method described above in the presence of a base.

[Chemical Formula 12]

<Isomerization Method>

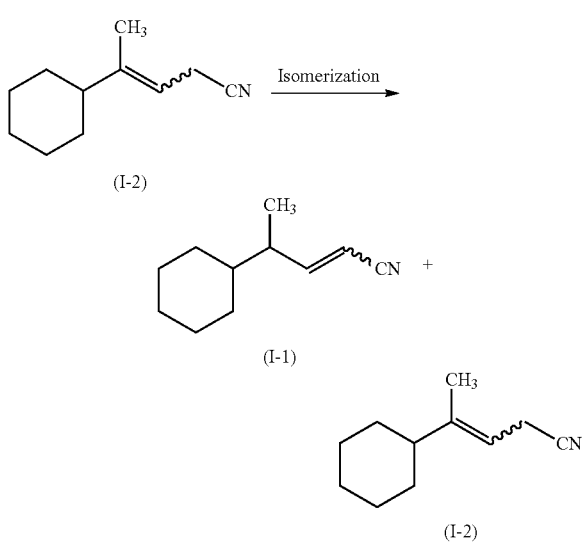

The bond represented by a wavy line in Formula (I-1) and Formula (I-2) indicates a cis form, a trans form, or a mixture of a cis form and a trans form.

Examples of the base to be used in this method include hydroxides of alkali metals or alkaline earth metals, carbonates of alkali metals or alkaline earth metals, alkoxides of alkali metals or alkaline earth metals, organic amines, etc. In terms of the yield, reaction activity, and handling, the base is preferably a hydroxide of an alkali metal or an alkaline earth metal or an alkoxide of an alkali metal or an alkaline earth metal, more preferably a hydroxide of an alkali metal or an alkoxide of an alkali metal, and further preferably an alkoxide of an alkali metal.

Examples of the hydroxide of an alkali metal or an alkaline earth metal include lithium hydroxide, sodium hydroxide, potassium hydroxide, barium hydroxide, etc. In terms of the yield, reaction activity, and handling, it is preferably sodium hydroxide or potassium hydroxide, more preferably potassium hydroxide.

The alkoxide of an alkali metal or an alkaline earth metal is preferably an alkoxide having 1 to 6 carbon atoms, more preferably an alkoxide having 1 to 4 carbon atoms. Specific examples thereof include sodium methoxide, sodium ethoxide, potassium methoxide, potassium ethoxide, sodium propoxide, potassium propoxide, sodium isopropoxide, potassium isopropoxide, sodium butoxide, potassium butoxide, sodium isobutoxide, potassium isobutoxide, sodium tert-butoxide, potassium tert-butoxide, etc. In terms of the yield, reaction activity, and handling, it is preferably sodium methoxide, sodium ethoxide, potassium methoxide, potassium ethoxide, or potassium tert-butoxide, more preferably sodium methoxide or potassium tert-butoxide.

The amount of the base to be used is, with respect to the 4-cyclohexyl-3-pentenenitrile (I-2), preferably 0.001 to 10 times by mole, more preferably 0.005 to 5 times by mole in terms of the yield, and further preferably 0.01 to 2 times by mole in terms of the yield and cost.

In terms of suppressing the decomposition of a substrate and improving the selectivity and yield, the reaction temperature is preferably −80 to 120° C., more preferably −20 to 80° C., and further preferably 0 to 50° C.

In this reaction, it is preferable to use a solvent in terms of the yield, selectivity, and handling. Examples of the solvent include hydrocarbons, halogenated solvents, ethers, ketones, esters, alcohols, dimethyl sulfoxide, dimethylformamide, dimethylacetamide, etc. Among these, alcohols are preferable since they are inactive to the reaction and easy to handle. The solvent is preferably methanol, ethanol, propanol, isopropanol, butanol, sec-butanol, or tert-butanol, more preferably methanol, ethanol, isopropanol, or tert-butanol, and further preferably methanol or tert-butanol.

The reaction pressure can be under atmospheric pressure. However, in order to obtain sufficient reaction temperature and reactivity, the reaction may be carried out under pressure, for example, at 0.1 to 20 MPa.

In terms of improving the quality as a fragrance material, it is preferable that a mixture of the 4-cyclohexyl-2-pentenenitrile (I-1) and the 4-cyclohexyl-3-pentenenitrile (I-2) obtained herein be purified by, for example, extraction, distillation, or silica gel column chromatography.

Method of Producing 4-Cyclohexylpentanenitrile (I-3)

Examples of the method of producing the 4-cyclohexylpentanenitrile (I-3) of the present invention include a method in which any one selected from the 4-cyclohexyl-2-pentenenitrile (I-1), the 4-cyclohexyl-3-pentenenitrile (I-2), and a mixture thereof is hydrogenated, a method in which 2-cyclohexylpropanal (II) is reacted with cyanoacetic acid in the presence of an activator and the condensate thus obtained is hydrogenated and further is decarboxylated, and a method in which 2-cyano-4-cyclohexyl pentanoate (VIII) is dealkoxycarbonylated. Among these, in terms of the reactivity, yield, and selectivity, the method is preferably a method in which any one selected from the 4-cyclohexyl-2-pentenenitrile (I-1), the 4-cyclohexyl-3-pentenenitrile (I-2), and a mixture thereof is hydrogenated and a method in which 2-cyano-4-cyclohexyl pentanoate (VIII) is dealkoxycarbonylated, more preferably a method in which the 4-cyclohexyl-2-pentenenitrile (I-1) or a mixture of the 4-cyclohexyl-2-pentenenitrile (I-1) and the 4-cyclohexyl-3-pentenenitrile (I-2) is hydrogenated and a method in which 2-cyano-4-cyclohexyl pentanoate (VIII) is dealkoxycarbonylated, and further preferably a method in which the 4-cyclohexyl-2-pentenenitrile (I-1) is hydrogenated and a method in which 2-cyano-4-cyclohexyl pentanoate (VIII) is dealkoxycarbonylated. In Formula (I-1) and Formula (I-2), the bond represented by a wavy line indicates a cis form, a trans form, or a mixture of a cis form and a trans form.

[Chemical Formula 13]

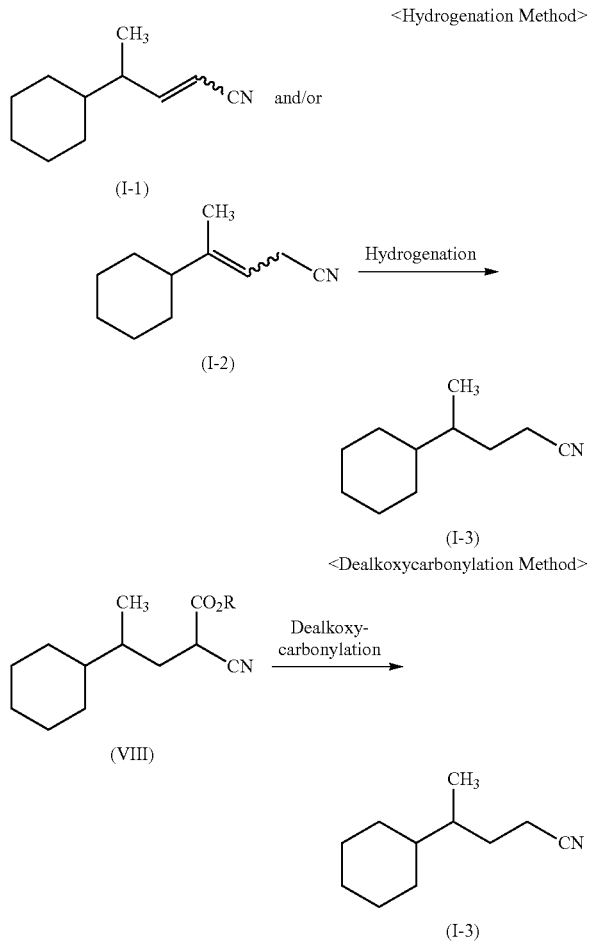

[In the formula, R indicates an alkyl group having 1 to 8 carbon atoms, an alkenyl group having 2 to 8 carbon atoms, or an alkyl group having 1 to 8 carbon atoms substituted with alkoxy having 1 to 8 carbon atoms.]

<Hydrogenation Method>

It is considered that the hydrogenation method is excellent in yield and selectivity because the 4-cyclohexyl-2-pentenenitrile (I-1) that is α,β-unsaturated nitrile is a conjugated nitrile, which tends to be subjected to a hydrogenation reaction.

In the hydrogenation reaction, it is preferable to use a hydrogenation catalyst. In terms of selectively hydrogenating an aliphatic double bond without affecting the nitrile group, the hydrogenation catalyst is, for example, preferably a transition metal such as palladium, platinum, ruthenium, or rhodium, and particularly, in terms of the reaction selectivity, more preferably palladium or platinum, further preferably palladium.

Examples of the hydrogenation catalyst include a homogeneous catalyst and a heterogeneous catalyst. It is preferably a heterogeneous catalyst, more preferably, for example, a heterogeneous catalyst with the above-mentioned transition metal being carried on a carrier.

Examples of the carrier include silica, alumina, silica alumina, zeolite, and carbon. In terms of the handling and reactivity, the carrier is more preferably silica, alumina, or carbon, further preferably carbon.

In the case of the heterogeneous catalyst, with respect to the 4-cyclohexyl-2-pentenenitrile (I-1), the 4-cyclohexyl-3-pentenenitrile (I-2), and a mixture thereof, the amount of the hydrogenation catalyst to be used including the carrier is preferably 0.001 to 100% by mass, and in terms of the reaction efficiency, more preferably 0.1 to 50% by mass. In the case of the homogeneous catalyst, with respect to the double bond to be reacted, the amount of the hydrogenation catalyst is preferably 0.0001 to 1 times by mole, and in terms of the reaction efficiency, more preferably 0.001 to 0.1 times by mole.

In the hydrogenation reaction, the reaction temperature is preferably 0 to 200° C., and in terms of the selectivity, more preferably 10 to 130° C., further preferably 20 to 80° C.

In the hydrogenation reaction, the hydrogen pressure is preferably from atmospheric pressure (0.1 MPa) to 20 MPa, and in terms of improving the reaction rate, more preferably 0.11 to 10 MPa.

In terms of the yield and selectivity, it is preferable to use a solvent for the hydrogenation reaction.

Examples of the solvent include hydrocarbons, halogenated solvents, ethers, ketones, esters, alcohols, dimethyl sulfoxide, dimethylformamide, and dimethylacetamide. Among these, alcohols and hydrocarbons are preferable since they are inactive to the reaction, and alcohols are further preferable.

Examples of the alcohols are preferably methanol, ethanol, propanol, isopropanol, butanol, sec-butanol, and tert-butanol, more preferably methanol, ethanol, and isopropanol.

<Dealkoxycarbonylation Method>

The dealkoxycarbonylation reaction can be carried out by a known method such as a two-step reaction method in which carboxylic acid obtained by hydrolyzing an ester is decarbonylated or a Krapcho reaction method in which an ester is directly dealkoxycarbonylated by one reaction operation. However, in terms of the reaction selectivity, operability, and waste reduction, the Krapcho reaction method is preferable.

Hereinafter, the Krapcho reaction method is described. It is preferable that this reaction be carried out in the coexistence of a salt in terms of promoting the reaction. Examples of the above-mentioned salt include halides of alkali metals such as sodium chloride, sodium bromide, sodium iodide, lithium chloride, and lithium iodide, cyanides of alkali metals such as sodium cyanide and potassium cyanide, and alkali metal salts or alkaline earth metal salts of organic acids such as sodium carbonate, potassium carbonate, sodium phosphate, sodium acetate, and potassium acetate. In terms of the reaction promoting effect and safety, a halide of an alkali metal, an alkali metal salt of an organic acid, and an alkaline earth metal salt of an organic acid are preferable, and in terms of the cost, sodium chloride, lithium chloride, sodium cyanide, sodium acetate, and potassium acetate are further preferable.

The amount of the salt to be used in the Krapcho reaction method is, with respect to the 2-cyano-4-cyclohexyl pentanoate (VIII), preferably 0.01 to 5 times by mole, and in terms of the yield and operability, more preferably 1 to 2 times by mole.

It is preferable that the Krapcho reaction method be carried out in a mixed solvent of water and a polar organic solvent in terms of promoting the reaction. The amount of water to be used is, with respect to the 2-cyano-4-cyclohexyl pentanoate (VIII), preferably 0.1 to 10 times by mole, more preferably 0.5 to 5 times by mole in terms of the yield, and further preferably 1 to 2 times by mole in terms of the production efficiency.

Examples of the polar organic solvent used in the Krapcho reaction method include dimethyl sulfoxide, N,N-dimethylformamide, N,N-dimethylacetamide, hexamethylphosphoric triamide, and hexamethylphosphorous triamide. In terms of the safety and handling, dimethyl sulfoxide and N,N-dimethylformamide are preferable. The amount of the organic solvent is, with respect to the 2-cyano-4-cyclohexyl pentanoate (VIII), preferably 1 to 1000% by mass, more preferably 10 to 500% by mass in terms of the yield, and further preferably 50 to 200% by mass in terms of the yield and production efficiency.

In the Krapcho reaction method, the reaction temperature is preferably 50 to 300° C. in terms of completing the reaction efficiently and suppressing side reactions, more preferably 100 to 200° C. in terms of the yield. Furthermore, when the reaction is carried out at a reaction temperature of 100° C. or more, a mixed solvent may be refluxed, or dropping water and distilling a mixture of water and alcohol produced as a byproduct in the dealkoxycarbonylation to the outside of the system may be carried out continuously.

In terms of improving the target odor and improving the quality as a fragrance material, it is preferable that, for example, the 4-cyclohexylpentanenitrile (I-3) obtained by the method described above be purified by extraction, distillation, or silica gel column chromatography.

Method of Producing 2-Cyano-4-Cyclohexyl Pentanoate (VIII)

As described above, 2-cyano-4-cyclohexyl pentanoate (VIII) can be obtained as follows. For example, 2-cyclohexylpropanal (II) is condensed with a compound of Formula (VI) (the Knoevenagel condensation), thereby 2-cyano-4-cyclohexylpenta-2-enoate (VII) is obtained, the 2-cyano-4-cyclohexylpenta-2-enoate (VII) is further hydrogenated, and thus, 2-cyano-4-cyclohexyl pentanoate (VIII) can be obtained (see Scheme).

Scheme

[Chemical Formula 14]

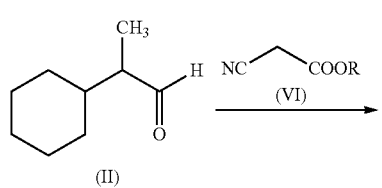

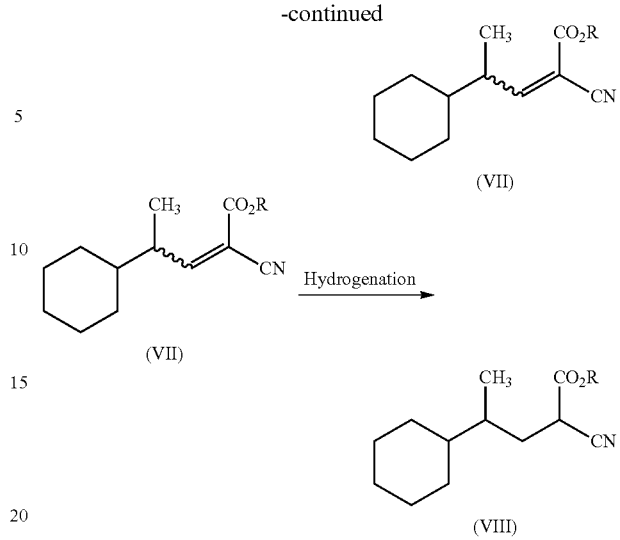

[In the formulae, R indicates an alkyl group having 1 to 8 carbon atoms, an alkenyl group having 2 to 8 carbon atoms, or an alkyl group having 1 to 8 carbon atoms substituted with alkoxy having 1 to 8 carbon atoms.]

In terms of the yield and selectivity, the method of producing the 2-cyano-4-cyclohexylpenta-2-enoate (VII) is preferably a method including a step of allowing 2-cyclohexylpropanal (II) and cyanoacetate (VI) to undergo Knoevenagel condensation, more preferably a step of condensing 2-cyclohexylpropanal (II) and cyanoacetate (VI) in the presence of an activator.

The ester portion (R in the formula above) of the cyanoacetate (VI) used in the Knoevenagel condensation is an alkyl group having 1 to 8 carbon atoms, an alkenyl group having 2 to 8 carbon atoms, or an alkyl group having 1 to 8 carbon atoms substituted with alkoxy having 1 to 8 carbon atoms. Examples of the alkyl group having 1 to 8 carbon atoms include linear or branched alkyl groups such as methyl, ethyl, propyl, butyl, pentyl, methylbutyl, hexyl, methylpentyl, ethylbutyl, heptyl, and octyl. Examples of the alkenyl group having 2 to 8 carbon atoms include methylene, ethylene, propylene, butylene, pentylene, hexylene, heptylene, and octylene. Examples of the alkoxy having 1 to 8 carbon atoms include linear or branched alkyloxy groups such as methoxy, ethoxy, propyloxy, butoxy, pentyloxy, methylbutyloxy, hexyloxy, methylpentyloxy, ethylbutyloxy, heptyloxy, and octyloxy. Examples of the alkyl group having 1 to 8 carbon atoms substituted with alkoxy having 1 to 8 carbon atoms include methoxymethyl, ethoxymethyl, and methoxyethyl. The ester portion (R in the formula above) of the cyanoacetate (VI) used in the Knoevenagel condensation is preferably a linear alkyl group having 1 to 4 carbon atoms and in terms of the cost and handling, further preferably a methyl group or an ethyl group.

Examples of the activator used in the Knoevenagel condensation reaction include organic amines or salts thereof, amino acids, and ammonium salts. It is preferably an organic amine or a salt thereof in terms of the yield and reaction activity, and particularly, more preferably an organic amine having 1 to 10 carbon atoms or an acetate thereof in terms of the reaction activity.

The amount of the activator to be used in the Knoevenagel condensation reaction is, with respect to the 2-cyclohexylpropanal (II), preferably 0.001 to 10 times by mole, more preferably 0.002 to 5 times by mole in terms of the yield, and further preferably 0.005 to 2 times by mole in terms of the yield and cost.

The amount of the cyanoacetate (VI) to be used with respect to the 2-cyclohexylpropanal (II) in the Knoevenagel condensation reaction is, with respect to the 2-cyclohexylpropanal (II), preferably 0.5 to 2 times by mole, more preferably 0.8 to 1.2 times by mole, and in terms of improving the yield, further preferably 1.01 to 1.10 times by mole.

In the Knoevenagel condensation reaction, the reaction temperature is preferably 0 to 150° C. in terms of the safety, preferably 20 to 150° C. in terms of the reaction efficiency, and more preferably 20 to 120° C. in terms of increasing the yield.

In the Knoevenagel condensation reaction, in terms of improving the reaction efficiency, it is preferable that the reaction be carried out while water produced as a byproduct by the reaction is removed. The method of removing water is preferably a method using a water scavenger (for example, a molecular sieve), a method in which water is distilled at normal pressure or under reduced pressure, or a method in which azeotropic dehydration is carried out under solvent reflux, with the solvent forming an azeotropic mixture with water. In terms of the efficiency and increasing the yield, it is preferably, for example, a method in which water is distilled under reduced pressure. In the method of removing water by azeotropic dehydration, the solvent to be used is preferably a solvent with a boiling point of 50 to 300° C. and, in terms of increasing the yield, more preferably a solvent with a boiling point of 70 to 250° C. Specifically, in the method of removing water by azeotropic dehydration, the solvent to be used is preferably a nonpolar hydrocarbon solvent such as benzene, toluene, xylene, cymene, or cyclohexane and in terms of the safety and easiness of solvent removal, more preferably toluene, xylene, or cyclohexane, further preferably toluene or cyclohexane.

The Knoevenagel condensation reaction is followed by hydrogenation and thereby 2-cyano-4-cyclohexyl pentanoate (VIII) is obtained. Examples of the hydrogenation method include a catalytic hydrogenation method using a hydrogenation catalyst and a hydride reduction method using a reducing agent such as sodium borohydride. However, in terms of the yield, a catalytic hydrogenation method is preferable.

<Catalytic Hydrogenation Method>

In terms of selectively hydrogenating an aliphatic double bond without affecting the nitrile group, the hydrogenation catalyst used in the catalytic hydrogenation method is, for example, preferably a transition metal such as palladium, platinum, ruthenium, or rhodium, and particularly, in terms of the reaction selectivity, more preferably palladium or platinum, further preferably palladium.

Examples of the hydrogenation catalyst include a homogeneous catalyst and a heterogeneous catalyst. It is preferably a heterogeneous catalyst, more preferably, for example, a heterogeneous catalyst with the above-mentioned transition metal being carried on a carrier.

Examples of the carrier include silica, alumina, silica alumina, zeolite, and carbon. In terms of the handling and reactivity, the carrier is more preferably silica, alumina, or carbon, further preferably carbon.

In the case of the heterogeneous catalyst, with respect to the 2-cyano-4-cyclohexylpenta-2-enoate (VII), the amount of the hydrogenation catalyst to be used including the carrier is preferably 0.001 to 100% by mass, and in terms of the reaction efficiency, more preferably 0.1 to 50% by mass. In the case of the homogeneous catalyst, with respect to the double bond to be reacted, the amount is preferably 0.0001 to 1 times by mole, and in terms of the reaction efficiency, more preferably 0.001 to 0.1 times by mole.

In the hydrogenation reaction, the reaction temperature is preferably 0 to 200° C., and in terms of the selectivity, more preferably 10 to 130° C., further preferably 20 to 80° C.

In the hydrogenation reaction, the hydrogen pressure is preferably from atmospheric pressure (0.1 MPa) to 20 MPa, and in terms of improving the reaction rate, it is more preferably 0.11 to 10 MPa.

In terms of the yield and selectivity, it is preferable to use a solvent for the hydrogenation reaction.

Examples of the solvent include hydrocarbons, halogenated solvents, ethers, ketones, esters, alcohols, dimethyl sulfoxide, dimethylformamide, and dimethylacetamide. Among these, alcohols and hydrocarbons are preferable since they are inactive to the reaction, and alcohols are further preferable.

Examples of the alcohols are preferably methanol, ethanol, propanol, isopropanol, butanol, sec-butanol, and tert-butanol, more preferably methanol, ethanol, and isopropanol.

<Hydride Reduction Method>

An example of the reducing agent used in a hydride reduction method is preferably sodium borohydride in terms of selectively hydrogenating a conjugated double bond without affecting the nitrile group or the ester group.

The amount of the reducing agent to be used in the hydride reduction method is, with respect to the 2-cyano-4-cyclohexylpenta-2-enoate (VII), preferably 0.25 to 2 times by mole in terms of the reaction yield and selectivity, more preferably 0.4 to 0.8 times by mole in terms of the economical efficiency and reactivity.

In terms of stabilization of the reducing agent, it is preferable to use a solvent for the hydride reduction reaction. Examples of the solvent used for the hydride reduction reaction include alkaline water, hydrocarbons, and ethers.

In the hydride reduction reaction, the reaction temperature is preferably 0 to 150° C., and in terms of the yield, more preferably 20 to 100° C., further preferably 30 to 80° C.

[Fragrance Composition]

The fragrance composition of the present invention contains a nitrile compound (I) of the present invention, preferably a mixture of 4-cyclohexyl-2-pentenenitrile (I-1) and 4-cyclohexyl-3-pentenenitrile (I-2). The amount of the nitrile compound (I) of the present invention to be contained in the fragrance composition is preferably 0.01 to 99% by mass, more preferably 0.1 to 15% by mass, and further preferably 0.3 to 3% by mass. When the nitrile compound (I) of the present invention is contained in an amount of 0.01 to 99% by mass, spicy-, green-, floral-, woody-, and citrus-like various odors are emphasized, which allows oil-, chemical-, and metallic-like undesirable odors to be suppressed.

Since the fragrance composition of the present invention contains a nitrile compound (I) of the present invention, it has a spicy tone, particularly a cumin-like odor, and when it is blended with other fragrances, spicy-, green-, floral-, woody-, and citrus-like various odors are emphasized, which allows oil-, chemical-, and metallic-like undesirable odors to be suppressed. Furthermore, the fragrance composition of the present invention is allowed to contain other fragrance components that are commonly used or blended fragrances with desired compositions, as other fragrances, in addition to the nitrile compound (I) of the present invention, which allows the fragrance composition to be provided with odors with, for example, a floral tone, a fruity tone, a herbal tone, a spicy tone, a green tone, a woody tone, or a balsamic tone. It is preferable that the above-mentioned other fragrances contain at least one selected from fragrances with a spicy-like odor, a green-like odor, a floral-like odor, a woody-like odor, and a citrus-like odor.

Furthermore, in the fragrance composition of the present invention, other fragrances that can be used in combination with the nitrile compound (I) of the present invention are preferably at least one selected from hydrocarbons, alcohols, phenols, aldehydes, ketones, acetals, ethers, esters, carbonates, lactones, oximes, nitriles, Schiff bases, amides, natural essential oils, and natural extracts, and among these, more preferably at least one selected from alcohols, aldehydes, esters, and lactones.

Hereinafter, the "plural notation" of each fragrance denotes a single compound or a mixture of at least two compounds.

Examples of hydrocarbons include limonene, α-pinene, β-pinene, terpinene, p-cymene, cedrene, longifolene, valencene, camphene, and myrcene.

Examples of alcohols include aliphatic alcohols, terpene-based alcohols, and aromatic alcohols.

Examples of aliphatic alcohols include prenol, trans-2-hexenol, cis-3-hexenol, 2,6-dimethylheptanol, 1-octen-3-ol, 3,6-nonadiene-1-ol, Undecavertol (Trade Name of Givaudan, 4-methyl-3-decene-5-ol), 2,4-dimethyl-3-cyclohexene-1-methanol, isocyclogeraniol, 2-tert-butylcyclohexanol, 4-tert-butylcyclohexanol, Mayol (Trade Name of Firmenich, 4-(1-methylethyl)-cyclohexanemethanol), Amber Core (Trade Name of Kao Corporation, 1-(2-tert-butyl cyclohexyl)-2-butanol), Timberol (Trade Name of Symrise, 1-(2,2,6-trimethylcyclohexyl)hexan-3-ol), Sandalmysore Core (Trade Name of Kao Corporation, 2-methyl-4-(2,2,3-trimethyl-3-cydopenten-1-yl)-2-buten-1-ol), Bacdanol (Trade Name of IFF, 2-ethyl-4-(2,2,3-trimethyl-3-cydopenten-1-yl)-2-buten-1-ol), and Florosa (Trade Name of Givaudan, 4-methyl-2-(2-methylpropyl)tetrahydro-2H-4-pyranol).

Examples of terpene-based alcohols include citronellol, hydroxycitronellol, linalool, dihydrolinalool, tetrahydrolinalool, ethyllinalool, geraniol, nerol, myrcenol, dihydromyrcenol, tetrahydromyrcenol, ocimenol, menthol, borneol, farnesol, nerolidol, cedrol, terpineol, and fenchyl alcohol.

Examples of aromatic alcohols include benzyl alcohol, phenylethyl alcohol, cumic alcohol, dimethyl phenyl ethyl carbinol, cinnamic alcohol, Phenyl Hexanol (Trade Name of Kao Corporation), Pamplefleur (Trade Name of IFF, 4-phenylpentanol), and Majantol (Trade Name of Symrise, 2,2-dimethyl-3-(3-methylphenyl)propanol).

Examples of phenols include anethole, guaiacol, eugenol, and isoeugenol.

Examples of aldehydes include aliphatic aldehyde, terpene aldehyde, and aromatic aldehyde as in the case of the aforementioned alcohols. All the aldehydes in which only the functional group of the fragrance component alcohols has been converted are included in the examples of the fragrance components.

Examples of other aldehydes include Aldehyde C-6 (Trade Name of Kao Corporation, 1-hexanal), Aldehyde C-8 (Trade Name of Kao Corporation, 1-octanal), Aldehyde C-9 (Trade Name of Kao Corporation, 1-nonanal), Aldehyde C-10 (Trade Name of Kao Corporation, 1-decanal), Aldehyde C-11 UNDECYL (Trade Name of Kao Corporation, undecynal), Aldehyde C-11 MOA (Trade Name of Symrise, 2-methyl decanal), Aldehyde C-111 LEN (Trade Name of Kao Corporation, 10-undecenal), Aldehyde C-12 LAURYL (Trade Name of Kao Corporation, 1-dodecanal), Aldehyde C-12 MNA (Trade Name of Kao Corporation, 2-methyl undecanal), Floral Super (Trade Name of IFF, 4,8-dimethyl-4,9-decadienal), Pollenal II (Trade Name of Kao Corporation, 2-cyclohexylpropanal), Myrac Aldehyde (Trade Name of IFF, 4(3)-(4-methyl-3-pentene-1-yl)-3-cyclohexene-1-carboxaldehyde), Lyral (Trade Name of IFF, 4(3)-(4-hydroxy-4-methylpentyl)-3-cyclohexene-1-carboxaldehyde), Cetonal (Trade Name of Givaudan, trimethyl cyclohexen methylbutanal), Vernaldehyde (Trade Name of Givaudan, 1-methyl-4-(4-methylpentyl)-3-cyclohexene carboxaldehyde), Melozone (Trade Name of IFF, octahydro-4,7-methanoindenecarboxaldehyde), Scentenal (Trade Name of Firmenich, methoxydicyclopentadiene carboxaldehyde), Dupical (Trade Name of Givaudan, 4-tricyclodecylidenebutanal), Bergamal (Trade Name of IFF, 3,7-dimethyl-2-methylene-6-octenal), campholenic aldehyde, Bourgeonal (Trade Name of Givaudan, 3-(4-tert-butylphenyl)propanal), Cyclamen Aldehyde (Trade Name of Givaudan, 3-(4-isopropylphenyl)-2-methylpropionaldehyde), Floralozone (Trade Name of IFF, 3-(4-ethylphenyl)-2,2-dimethylpropionaldehyde, p-ethyl-2,2-dimethyl-hydrocinnamaldehyde), Suzaral (Trade Name of Takasago International Corporation), 3-(4-isobutylphenyl)-2-methylpropionaldehyde), Lilyall (Trade Name of Givaudan, 3-(4-t-butylphenyl)-2-methyl propionaldehyde, p-tert-butyl-alpha-methylhydrocinnamic aldehyde), Amyl Cinnamic Aldehyde (Trade Name of Kao Corporation), Hexyl Cinnamic Aldehyde (Trade Name of Kao Corporation, 2-n-hexyl-3-phenyl-2-propenal), Canthoxal (Trade Name of IFF, 2-methyl-3-(4-methoxyphenyl)propanal), vanillin, ethyl vanillin, Heliotropine (Trade Name of Takasago International Corporation, 3,4-methylenedioxybenzaldehyde), Helional (Trade Name of IFF, α-methyl-1,3-benzodioxole-5-propanal, 2-methyl-3-(3,4-methylenedioxyphenyl)-propanal), Triplal (Trade Name of IFF, 2,4-dimethyl-3-cyclohexane-1-carboxaldehyde), and 2,6-nonadienal.

Examples of ketones include methyl heptenone, dimethyl octenone, hexylcyclopentanone, dihydrojasmone, Veloutone (Trade Name of Firmenich, 2,2,5-trimethyl-5-pentylcydopentanone), Nectaryl (Trade Name of Givaudan, 2-(2-(4-methyl-3-cyclohexen-1-yl)propyl)cydopentanone), ionone, methylionone, γ-methylionone, damascone, α-damascone, δ-damascone, damascenone, Dynascone (Trade Name of Firmenich, 1-(5,5-dimethyl-1-cyclohexen-1-yl)-4-penten-1-one), irone, Cashmeran (Trade Name of IFF, 1,2,3,5,6,7-hexahydro-1,1,2,3,3-pentamethyl-4H-inden-4-one), Iso E Super (Trade Name of IFF, 1-(1,2,3,4,5,6,7,8-octahydro-2,3,8,8-tetramethyl-2-naphthalenyl)-ethan-1-one), Calone (Trade Name of Firmenich, 7-methyl-3,5-dihydro-2H-benzodioxepin-3-one), carvone, menthone, acetyl cedrene, isolongifolanone, nootkatone, raspberry ketone, benzophenone, Tonalid (Trade Name of PFW, 6-acetyl-1,1,2,4,4,7-hexamethyl tetrahydronaphthalene), muscone, Muscenone (Trade Name of Firmenich, 3-methyl-5-cyclopentadecen-1-one), civetone, Globanone (Trade Name of Symrise, 8-cyclohexadecenone), ethyl maltol, camphor, and Isodamascone (Trade Name of Symrise, 1-(2,4,4-trimethyl-2-cyclohexyl)-trans-2-butanone).

Examples of acetals include Anthoxan (Trade Name of Kao Corporation), Boisambrene Forte (Trade Name of Kao Corporation), Troenan (Trade Name of Kao Corporation), Methyl Pamplemousse (Trade Name of Givaudan, 1,1-dimethoxy-2,2,5-trimethyl-4-hexene), citral dimethyl acetal, hydratropaldehyde dimethyl acetal, Verdoxan (Trade Name of Kao Corporation), acetaldehyde ethyl linalyl acetal, and Floropal (Trade Name of Symrise, 2,4,6-trimethyl-2-phenyl-1,3-dioxane).

Examples of ethers include Herbavert (Trade Name of Kao Corporation), cedryl methyl ether, Ambroxan (Trade Name of Kao Corporation, [3aR-(3a.α,5a.β,9a.α,9b.β)] dodecahydro-3a,6,6,9a-tetramethyl naphto[2,1-b]furan), Ambrotech (Trade Name of Kao Corporation, dodecahydro-3a,6,6,9a-tetramethylnaphtho[2,1-b]furan), methyl isoeugenol, citronellyl ethyl ether, geranyl ethyl ether, 1,8-cineole, rose oxide, estragole, anethole, hinokitiol, β-naphthol methyl ether, β-naphthol ethyl ether, and Galaxolide (Trade Name of IFF, 1,3,4,6,7,8-hexahydro-4,6,6,7,8,8-hexamethylcyclopenta-γ-2-benzopyran).

Examples of esters to be used as a fragrance material include ester of aliphatic carboxylic acid, ester of aromatic carboxylic acid, and ester of other carboxylic acid.

Examples of aliphatic carboxylic acids that form ester of aliphatic carboxylic acid include linear and branched carboxylic acids having 1 to 18 carbon atoms. Among these, carboxylic acids having 1 to 6 carbon atoms such as formic acid, acetic acid, and propionic acid are important, and particularly acetic acid is important. Examples of aromatic carboxylic acids that form ester of aromatic carboxylic acid include benzoic acid, anisic acid, phenylacetic acid, cinnamic acid, salicylic acid, and anthranilic acid. Examples of alcohols that form esters of aliphatic and aromatic acid include linear and branched aliphatic alcohols having 1 to 5 carbon atoms and the above-mentioned fragrance component alcohols.

Examples of esters of other carboxylic acid include Ethyl Safranate (Trade Name of Givaudan, ethyl dihydrocyclo geranate), Poirenate (Trade Name of Kao Corporation), Fruitate (Trade Name of Kao Corporation, ethyl tricyclo [$5.2.1.0^{2.6}$] decan-2-carboxylate), methyl jasmonate, MDJ (Trade Name of Kao Corporation, methyl dihydrojasmonate, methyl (2-pentyl-3-oxocyclopentyl)acetate), tricyclodecenyl propionate, and ethyl-3-methyl-3-phenylglycidate (Common Name; Aldehyde C-16).

Examples of carbonates include Liffarome (Trade Name of IFF, cis-3-hexenyl methyl carbonate), Jasmacyclat (Trade Name of Kao Corporation), and Floramat (Trade Name of Kao Corporation).

Examples of lactones include γ-nonalactone, γ-decalactone, δ-decalactone, Jasmolactone (Trade Name of Firmenich, tetrahydro-6-(3-hexenyl)-2H-pyran-2-one), γ-undecalactone, coumarin, octahydrocoumarin, Florex (Trade Name of Firmenich, 6-ethylideneoctahydro-5,8-methano-2H-1-benzopyran-2-one), cyclopentadecanolide, Habanolide (Trade Name of Firmenich, 12(11)-oxacyclohexadecen-2-one), Ambrettolide (Trade Name of IFF, 10-octacycloheptadecen-2-one), and ethylene brassylate.

Examples of oximes include Buccoxime (Trade Name of Symrise, 1,5-dimethyl-bicyclo[3,2,1]octan-8-one oxime), Labienoxime (Trade Name of Givaudan, 2,4,4,7-tetramethyl-6,8-nonadiene-3-one oxime), and 5-methyl-3-heptanone oxime.

Examples of nitriles include dodecanenitrile, citronellyl nitrile, cuminyl nitrile, cinnamyl nitrile, and Peonile (Trade Name of Givaudan, 2-cyclohexylidene-2-phenylacetonitrile).

Examples of Schiff bases include Aurantiol (Trade Name of Givaudan, methyl N-(3,7-dimethyl-7-hydroxyoctylidene)-anthranilate) and Ligantral (Trade Name of Givaudan, methyl (3,5-dimethyl-3-cyclohexene-1-yl)methyleneanthranilate).

Examples of amides include Gardamide (Trade Name of Givaudan, N,2-dimethyl-N-phenylbutyramide) and Paradisamide (Trade Name of Givaudan, 2-ethyl-N-methyl-N-(3-methylphenyl)butanamide).

Examples of the natural essential oils and the natural extracts include orange, lemon, lime, bergamot, vanilla, mandarin, peppermint, spearmint, lavender, chamomile, rosemary, eucalyptus, sage, basil, rose, rockrose, geranium, jasmine, ylang ylang, anise, clove, ginger, nutmeg, cardamon, cedar, cypress, vetiver, patchouli, lemongrass, labdanum, galbanum, petitgrain, and olibanum.

These other fragrances can be selected suitably depending on, for example, the type of the blended fragrance as well as the type and intensity of intended odor. However, the amount of each of them contained in the fragrance composition is preferably 0.0001 to 99.99% by mass, more preferably 0.001 to 80% by mass. The total amount of them contained in the fragrance composition is preferably 5 to 99.99% by mass, more preferably 50 to 99.9% by mass.

The fragrance composition of the present invention can contain an oil, which itself has no odor, to be used as a base that allows the nitrile compound (I) of the present invention and other fragrance materials to be contained therein. Such an oil allows a fragrance component to be mixed uniformly, to be easily mixed into a product, and to be easily provided with a suitable intensity of fragrance. Examples of the oil include polyhydric alcohols such as ethylene glycol, propylene glycol, butylene glycol, and dipropylene glycol, esters such as isopropyl myristate, dibutyl adipate, and diethyl sebacate, hydrocarbons such as liquid paraffin and squalane, and surfactants such as polyoxyethylene alkyl ether and ester of sorbitan fatty acid.

Among these, in terms of the solubility of all the fragrance components, the oil is preferably polyhydric alcohol or ester, more preferably dipropylene glycol or isopropyl myristate. The amount of such an oil to be contained in the fragrance composition is preferably 0.01 to 95% by mass, more preferably 0.1 to 90% by mass, further preferably 1 to 80% by mass, and even more preferably 5 to 80% by mass.

The fragrance composition of the present invention also provides an effect of further emphasizing spicy-, green-, floral-, woody-, and citrus-like various odors in addition to the odor of the nitrile compound (I) of the present invention, which allows oil-, chemical-, and metallic-like undesirable odors to be suppressed. Such a fragrance composition can be used suitably to provide fragrances for cosmetics, cleaner compositions, etc.

[Use as Fragrance Component]

The fragrance composition containing a nitrile compound (I) of the present invention can be used, as a fragrance component for various types of products, as a blended fragrance with a preferable fragrance note that is provided with a spicy tone, particularly a cumin-like odor and that further emphasizes spicy-, green-, floral-, woody-, and citrus-like various odors, which allows oil-, chemical-, and metallic-like undesirable odors to be suppressed. Therefore, the present invention is a method of using a nitrile compound (I) of the present invention as a fragrance component, preferably a method of using a nitrile compound (I) of the present invention as a fragrance component for a fragrance composition, a cleaner composition, a softener composition, or a cosmetic. For the method of using said compound, it can be contained, alone or in combination with other components, in the bases of toiletry products such as soaps, cosmetics, hair cosmetics, detergents, softeners, spray products, air fresheners, perfumes, and bath agents.

Particularly, since the nitrile compound (I) of the present invention is stable in an aqueous vehicle, and is used for applications in which spicy-, green-, floral-, woody-, and citrus-like fragrance notes are used preferably, it is used for preferably cleaner compositions, softener compositions, and cosmetics, more preferably cleaner compositions.

Accordingly, the present invention also provides a cleaner composition, a softener composition, and a cosmetic that each contain a fragrance composition of the present invention.

The cleaner composition of the present invention is preferably a cleaner composition for hard surfaces, a cleaner composition for clothing, or a body cleaner composition, more preferably a cleaner composition for hard surfaces.

Examples of the cleaner composition for hard surfaces include an all purpose cleaner and a dish cleaner composition.

Examples of the body cleaner composition include a skin cleaner composition and a hair cleaner composition. It is preferably a hair cleaner composition.

The cosmetic of the present invention is preferably a perfume.

It is preferable that the cleaner composition of the present invention contain an anionic surfactant in addition to the nitrile compound (I) of the present invention. Furthermore, a nonionic surfactant, a pH adjuster, a viscosity modifier, a solvent, an oil, a preservative, water, etc. can be blended thereinto.

It is preferable that the softener composition of the present invention contain a cationic surfactant in addition to the nitrile compound (I) of the present invention. Furthermore, a pH adjuster, a solvent, an oil, a preservative, water, etc. can be blended thereinto.

In the perfume of the present invention, a solvent, water, etc. can be blended thereinto in addition to the nitrile compound (I) of the present invention.

With respect to the above-described embodiment, the present invention further discloses a nitrile compound and a method of producing a nitrile compound.

<1> A nitrile compound represented by Formula (I-3), Formula (I-2), or Formula (I-1), preferably nitrile compounds represented by Formula (I-2) and Formula (I-3), and more preferably a nitrile compound represented by Formula (I-3).

[Chemical Formula 15]

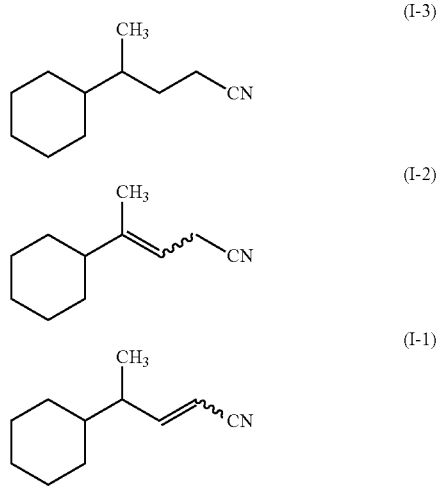

The bond represented by a wavy line in Formula (I-1) and Formula (I-2) indicates a cis form, a trans form, or a mixture of a cis form and a trans form.

<2> A fragrance composition, containing a nitrile compound according to the item <1>.

<3> A fragrance composition, containing a nitrile compound, wherein the nitrile compound is a mixture of 4-cyclohexyl-2-pentenenitrile represented by Formula (I-1) below and 4-cyclohexyl-3-pentenenitrile represented by Formula (I-2) below.

[Chemical Formula 16]

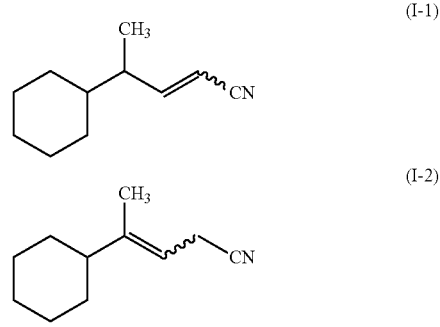

The bond represented by a wavy line in Formula (I-1) and Formula (I-2) indicates a cis form, a trans form, or a mixture of a cis form and a trans form.

<4> The fragrance composition according to the item <2> or <3>, further containing at least one selected from fragrances having a spicy-like odor, a green-like odor, a floral-like odor, a woody-like odor, and a citrus-like odor.

<5> The fragrance composition according to the item <2> or <3>, further containing a fragrance in addition to the nitrile compound, wherein the fragrance contained in addition to the nitrile compound contains at least one selected from hydrocarbons, alcohols, phenols, aldehydes, ketones, acetals, ethers, esters, carbonates, lactones, oximes, nitriles, Schiff bases, natural essential oils, and natural extracts.

<6> A cleaner composition, containing a fragrance composition according to any one of the items <2> to <5>.

<7> A softener composition, containing a fragrance composition according to any one of the items <2> to <5>.

<8> A cosmetic, containing a fragrance composition according to any one of the items <2> to <5>.

<9> A method of using a nitrile compound according to the item <1> as a fragrance component for a fragrance composition, a cleaner composition, a softener composition, or a cosmetic.

<10> A method of producing 4-cyclohexyl-2-pentenenitrile represented by Formula (I-1) below, including a step of condensing 2-cyclohexylpropanal represented by Formula (II) below and a cyanomethyl phosphonic acid derivative (III), preferably including a step of condensing 2-cyclohexylpropanal represented by Formula (II) below and a cyanomethyl phosphonic acid derivative (III) in the presence of an activator.

[Chemical Formula 17]

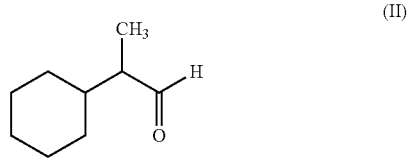

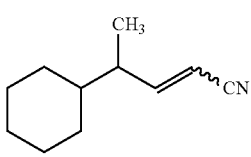

(I-1)

The bond represented by a wavy line in Formula (I-1) indicates a cis form, a trans form, or a mixture of a cis form and a trans form.

<11> The method of producing 4-cyclohexyl-2-pentenenitrile represented by Formula (I-1) according to the item <10>, wherein the cyanomethyl phosphonic acid derivative (III) is ester of cyanomethylphosphonic acid represented by Formula (III-A) or cyanomethyl phosphonium salt represented by Formula (III-B), preferably diester of cyanomethylphosphonic acid (III-A).

[Chemical Formula 18]

(III-A)

$$\text{RO}\underset{\text{RO}}{\overset{\text{O}}{\|}}\text{P}-\text{CN}$$

(III-B)

$$\underset{R}{\overset{R}{|}}\text{R}-\overset{+}{\text{P}}-\text{CN} \quad X^{\ominus}$$

[In the formulae, R indicates an alkyl group or phenyl group having 1 to 6 carbon atoms, preferably a linear or branched alkyl group or phenyl group having 1 to 6 carbon atoms, more preferably a linear or branched alkyl group having 1 to 3 carbon atoms, and further preferably a methyl group or an ethyl group, while X indicates a halogen atom (an iodine atom, a bromine atom, a chlorine atom, or a fluorine atom).]

<12> A method of producing 4-cyclohexyl-3-pentenenitrile represented by Formula (I-2) below, including a step of condensing 2-cyclohexylpropanal represented by Formula (II) below and cyanoacetic acid represented by Formula (IV) below and a step of decarboxylating a condensate thus obtained, preferably including a step of condensing 2-cyclohexylpropanal (II) and cyanoacetic acid (IV) in the presence of an activator and a step of decarboxylating a condensate thus obtained.

[Chemical Formula 19]

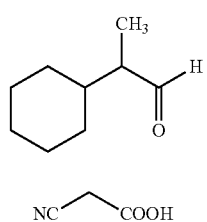

(II)

NC—COOH (IV)

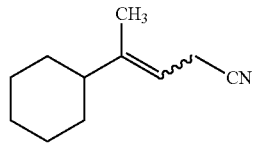

(I-2)

In Formula (I-2), the bond represented by a wavy line indicates a cis form, a trans form, or a mixture of a cis form and a trans form.

<13> A method of producing a mixture of 4-cyclohexyl-2-pentenenitrile represented by Formula (I-1) below and 4-cyclohexyl-3-pentenenitrile represented by Formula (I-2) below, including a step of condensing 2-cyclohexylpropanal represented by Formula (II) below and acetonitrile represented by Formula (V) below, preferably including a step of condensing 2-cyclohexylpropanal (II) and acetonitrile (V) in the presence of an activator.

[Chemical Formula 20]

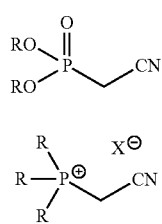

(II)

CH₃CN (V)

(I-1)

(I-2)

In Formula (I-1) and Formula (I-2), the bond represented by a wavy line indicates a cis form, a trans form, or a mixture of a cis form and a trans form.

<14> A method of producing a mixture of 4-cyclohexyl-2-pentenenitrile represented by Formula (I-1) below and 4-cyclohexyl-3-pentenenitrile represented by Formula (I-2) below, including a step of isomerizing the 4-cyclohexyl-3-pentenenitrile represented by Formula (I-2) below, preferably including a step of isomerizing the 4-cyclohexyl-3-pentenenitrile (I-2) obtained by the method described above in the presence of a base.

[Chemical Formula 21]

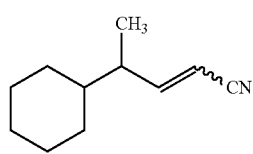

(I-1)

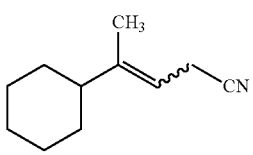
(I-2)

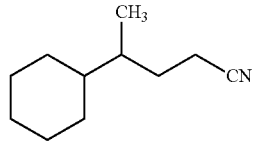
(I-3)

In Formula (I-1) and Formula (I-2), the bond represented by a wavy line indicates a cis form, a trans form, or a mixture of a cis form and a trans form.

<15> A method of producing 4-cyclohexylpentanenitrile represented by Formula (I-3) below, including hydrogenating any one selected from 4-cyclohexyl-2-pentenenitrile represented by Formula (I-1) below, 4-cyclohexyl-3-pentenenitrile represented by Formula (I-2) below, and a mixture of the 4-cyclohexyl-2-pentenenitrile represented by Formula (I-1) below and the 4-cyclohexyl-3-pentenenitrile represented by Formula (I-2) below, preferably hydrogenating any one of them using a hydrogenation catalyst.

[Chemical Formula 22]

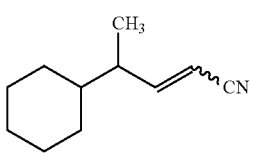
(I-1)

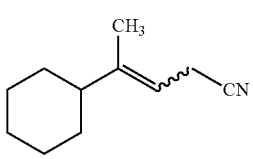
(I-2)

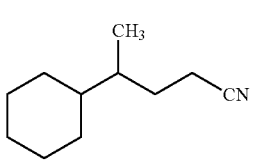
(I-3)

In Formula (I-1) and Formula (I-2), the bond represented by a wavy line indicates a cis form, a trans form, or a mixture of a cis form and a trans form.

<16> A method of producing 4-cyclohexylpentanenitrile (I-3), including dealkoxycarbonylating 2-cyano-4-cyclohexyl pentanoate represented by Formula (VIII) below to obtain 4-cyclohexylpentanenitrile (I-3).

[Chemical Formula 23]

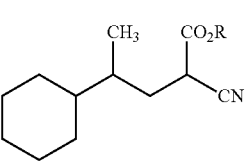
(VIII)

In the formula, R indicates an alkyl group having 1 to 8 carbon atoms, an alkenyl group having 2 to 8 carbon atoms, or an alkyl group having 1 to 8 carbon atoms substituted with alkoxy having 1 to 8 carbon atoms.

<17> The method of producing 4-cyclohexylpentanenitrile (I-3) according to the item <16>, wherein the dealkoxycarbonylation is carried out by a Krapcho reaction method or a two-step reaction method in which carboxylic acid obtained by hydrolyzing the 2-cyano-4-cyclohexyl pentanoate represented by Formula (VIII) is decarbonylated.

<18> The method of producing 4-cyclohexylpentanenitrile (I-3) according to the item <16>, wherein the dealkoxycarbonylation is carried out by a Krapcho reaction method in the presence of a salt.

<19> The method of producing 4-cyclohexylpentanenitrile (I-3) according to the item <18>, wherein the Krapcho reaction method is carried out in a mixed solvent of water and a polar organic solvent.

<20> The method of producing 4-cyclohexylpentanenitrile (I-3) according to any one of the items <16> to <19>, further including a step of hydrogenating 2-cyano-4-cyclohexylpenta-2-enoate represented by Formula (VII) below to obtain 2-cyano-4-cyclohexyl pentanoate represented by Formula (VIII).

[Chemical Formula 24]

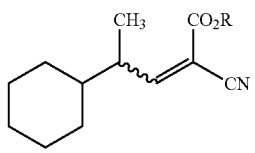
(VII)

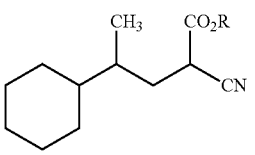
(VIII)

In Formula (VII), the bond represented by a wavy line indicates a cis form, a trans form, or a mixture of a cis form and a trans form.

In the formulae, R indicates an alkyl group having 1 to 8 carbon atoms, an alkenyl group having 2 to 8 carbon atoms, or an alkyl group having 1 to 8 carbon atoms substituted with alkoxy having 1 to 8 carbon atoms.

<21> The method of producing 4-cyclohexylpentanenitrile (I-3) according to the item <20>, wherein the hydrogenation is carried out by a catalytic hydrogenation method using a hydrogenation catalyst or a hydride reduction method using a reducing agent.

<22> The method of producing 4-cyclohexylpentanenitrile (I-3) according to the item <20> or <21>, further including a step of condensing 2-cyclohexylpropanal represented by Formula (II) below with a compound represented by Formula (VI) below (Knoevenagel condensation) to obtain the 2-cyano-4-cyclohexylpenta-2-enoate represented by Formula (VII).

[Chemical Formula 25]

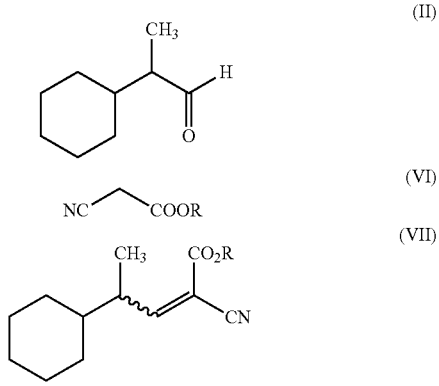

In Formula (VII), the bond represented by a wavy line indicates a cis form, a trans form, or a mixture of a cis form and a trans form.

In the formulae, R indicates an alkyl group having 1 to 8 carbon atoms, an alkenyl group having 2 to 8 carbon atoms, or an alkyl group having 1 to 8 carbon atoms substituted with alkoxy having 1 to 8 carbon atoms.

<23> The method of producing 4-cyclohexylpentanenitrile (I-3) according to the item <22>, wherein the condensation is carried out in the presence of an activator.

<24> The method of producing 4-cyclohexylpentanenitrile (I-3) according to the item <22> or <23>, wherein the condensation is carried out while water produced as a byproduct by the reaction is removed.

EXAMPLES

The details of the measurement methods carried out in the following examples and comparative examples are described together below.

[Conversion Ratio and Reaction Yield]

The conversion ratio and reaction yield were determined by gas chromatography (GC) quantitative analysis.

<Apparatus for Gas Chromatography>

GC Apparatus: HP6850, manufactured by HEWLETT PACKARD

Column: DB-1 (with an inner diameter of 0.25 mm, a length of 30 m, and a film thickness of 0.25 μm), manufactured by J&W <Analytical Conditions>

Carrier Gas: He, 1.5 mL/min

Injection Condition: 280° C., Split Ratio: 1/100

Detection Condition: FID System, 280° C.

Column Temperature Condition: 100° C.→Raised at 10° C./min→Maintained at 300° C. for 10 minutes Internal Standard Compound: n-Dodecane

[Compound Identification]

Each compound obtained in the following production examples was identified by spectrum analyses using a nuclear magnetic resonance spectrum (Mercury 400, manufactured by Varian) ($^1$H-NMR, $^{13}$C-NMR) and a Fourier transform infrared spectrophotometer (FT-710, manufactured by HORIBA, Ltd.). The measurement conditions, etc. are described in each measurement result.

[Odor Evaluation]

Two experts who had an experience of at least five years but less than ten years as well as two experts who had an experience of at least 25 years of blending odors and evaluating fragrances determined the fragrance note and the intensity by a smelling strip method. About 5 mm of the end of each smelling strip (fragrance test paper with a width of 6 mm and a length of 150 mm) was immersed in a sample and thereby evaluation was performed.

With respect to odors, fragrances that are sensed mainly (main odors) were listed from the strongest to the weakest and further fragrances that are sensed secondarily (secondary odors) were noted.

The odor intensity was indicated by the relative evaluation, with 0 denoting odorless and 5 denoting very strong (a six grades odor intensity measurement method).

Production of Nitrile Compound

Example 1

Production of 4-Cyclohexyl-2-Pentenenitrile (I-1)

According to the following scheme, 2-cyclohexylpropanal (II) ("Pollenal II" (Trade Name), manufactured by Kao Corporation) and diethyl cyanomethyl phosphonate (III-1) were condensed and thereby 4-cyclohexyl-2-pentenenitrile (I-1) was obtained. In Formula (I-1), the bond represented by a wavy line indicates a cis form, a trans form, or a mixture of a cis form and a trans form.

Scheme

[Chemical Formula 26]

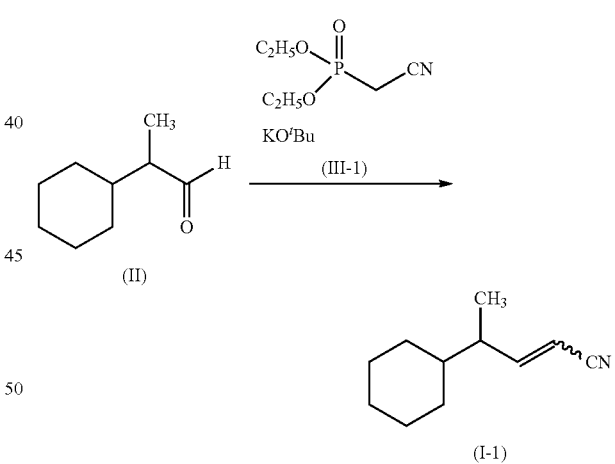

In a 300 mL flask, 10.1 g of potassium tert-butoxide (0.090 mole; 1.03 times by mole with respect to the diethyl cyanomethyl phosphonate (III-1)) and 150 g of toluene (1.58 moles; 17.4 times by mole with respect to the 2-cyclohexylpropanal (II)) were placed, which then was subjected to nitrogen substitution. Thereafter, 15.4 g of the diethyl cyanomethyl phosphonate (III-1) (0.087 mole; 1.00 times by mole with respect to the 2-cyclohexylpropanal (II)) was dropped thereinto at room temperature, which then was stirred for 15 minutes. Thereafter, this was cooled to 0° C. and then 12.2 g (0.087 mole) of the 2-cyclohexylpropanal (II) ("Pollenal II" (Trade Name), manufactured by Kao Corporation) was dropped thereinto. After this was stirred for five minutes, the temperature thereof was raised to room temperature and then it was reacted for 30 minutes. Gas chromatography analysis was carried out and as a result, the conversion ratio of the 2-cyclohexylpropanal (II) into 4-cyclohexyl-2-pentenenitrile (I-1) was 99.9%, and the reaction yield was 98.7%. After completion of the reaction, diethyl ether was added thereto, which then was washed twice with a saturated ammonium chloride aqueous solution and was subsequently washed with saturated brine. The aqueous layer was extracted by settled separation and then the organic layer was dried with magnesium sulfate, which then was filtered. Thereafter, the solvent was distilled, and thus a concentrated liquid was obtained. Subsequently, the concentrated liquid was purified by normal phase silica gel column chromatography with a 3 v/v % ethyl acetate/hexane solvent and then 12.5 g of colorless liquid was obtained by Kugelrohr distillation. The colorless liquid thus obtained was subjected to gas chromatography (GC) analysis. As a result, the 4-cyclohexyl-2-pentenenitrile (I-1) had a purity of 99.8%, an isolated yield of 84.5%, and a ratio of isomers of E-isomers:Z-isomers=40:60, which was determined from the GC area ratio.

The measurement results of each spectrum analysis and odor evaluation are indicated below.

(1) $^1$H-NMR (CDCl$_3$, 400 MHz); δ (ppm):
E-isomer; 0.81-1.07 (2H, m), 1.02 (3H, d, J=6.8 Hz), 1.09-1.31 (4H, m), 1.60-1.82 (5H, m), 2.14 (1, m), 5.25 (1H, d, J=16.4 Hz), 6.64 (1H, dd, J=16.4, 8.4 Hz).
Z-isomer; 0.81-1.07 (2H, m), 1.05 (3H, d, J=6.8 Hz), 1.09-1.31 (4H, m), 1.60-1.82 (5H, m), 2.57 (1H, m), 5.27 (1H, d, J=10.8 Hz), 6.31 (1H, dd, J=10.8, 10.4 Hz).

(2) $^{13}$C-NMR (CDCl$_3$, 100 MHz); δ (ppm):
30.5, 30.7, 30.8, 42.8, 42.9, 43.0, 43.9, 116.6, 117.9,
Identified E-Isomer; 16.4, 26.7, 98.9, 160.7,
Identified Z-Isomer; 17.7, 26.8, 98.5, 160.7.

(3) FT-IR (neat); cm$^{-1}$: 750, 891, 970, 1263, 1375, 1448, 1629, 2220, 2852, 2924.

(4) Odor: (Main Odor) Cumin (Secondary Odor) Green, Fruity Apple.

(5) Odor Intensity: 4.5.

Example 2

Production of 4-Cyclohexyl-3-Pentenenitrile (I-2)

According to the following scheme, 2-cyclohexylpropanal (II) ("Pollenal II" (Trade Name), manufactured by Kao Corporation) and cyanoacetic acid (IV) were condensed, which then was decarboxylated. Thus, 4-cyclohexyl-3-pentenenitrile (I-2) was obtained. In Formula (I-2), the bond represented by a wavy line indicates a cis form, a trans form, or a mixture of a cis form and a trans form.

Scheme

[Chemical Formula 27]

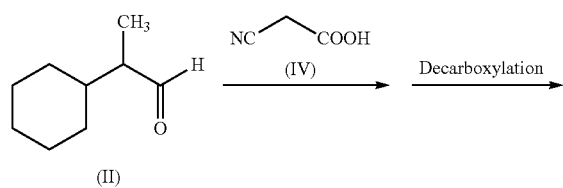

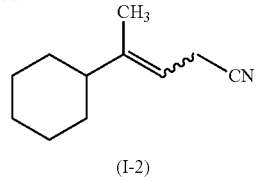

In a 1 L flask with a Dean-Stark dehydration tube attached thereto, 211.2 g (1.51 moles) of 2-cyclohexylpropanal (II) ("Pollenal II" (Trade Name), manufactured by Kao Corporation), 134.6 g of cyanoacetic acid (IV) (1.58 moles; 1.05 times by mole with respect to the 2-cyclohexylpropanal (II)), 6.0 g of ammonium acetate (0.078 mole; 0.0517 times by mole with respect to the 2-cyclohexylpropanal (II)), and 213.0 g of cyclohexane (2.53 moles; 100% by mass with respect to the 2-cyclohexylpropanal (II)) were placed, which then was subjected to nitrogen substitution. Thereafter, this was reacted for five hours while by-product water was distilled by azeotropic dehydration with cyclohexane under reflux (84° C.) while stirring. Then the reaction mixture was subjected to gas chromatography analysis. As a result, the conversion ratio of the 2-cyclohexylpropanal (II) into a condensate was 100% and the reaction yield was 92.7%. After completion of the reaction, ethyl acetate and saturated brine were added thereto, then the aqueous layer was extracted by settled separation, and the organic layer was washed with saturated brine. The solvent was distilled from the organic layer and thereby a concentrated liquid was obtained. Then 315.11 g of the aforementioned concentrated liquid was subjected to distillation purification involving decarboxylation at 153° C. under reduced pressure (2.6 kPa). Thus, 179.5 g of colorless liquid was obtained. The colorless liquid thus obtained was subjected to gas chromatography (GC) analysis. As a result, the 4-cyclohexyl-3-pentenenitrile (I-2) had a purity of 97.8%, an isolated yield of 71.5%, and a ratio of isomers of E-isomers:Z-isomers=75:25, which was determined from the GC area ratio.

The measurement results of each spectrum analysis and odor evaluation are indicated below.

(1) $^1$H-NMR (CDCl$_3$, 400 MHz); δ (ppm):
E-isomer; 1.14 (3H, m), 1.23 (3H, m), 1.61 (3H, s), 1.65 (2H, m), 1.73 (2H, m), 1.85 (1H, t, J=11.6 Hz), 3.00 (2H, d, J=6.8 Hz), 5.11 (1H, t, J=6.8 Hz).
Z-isomer; 1.15 (2H, m), 1.47 (2H, m), 1.63 (3H, s), 1.65 (4H, m), 1.73 (2H, m), 2.26 (1H, m), 3.03 (2H, d, J=7.2 Hz), 5.04 (1H, t, J=6.8 Hz).

(2) $^{13}$C-NMR (CDCl$_3$, 100 MHz); δ (ppm):
E-isomer; 15.2, 16.6, 26.6, 26.9, 31.9, 47.6, 110.2, 119.0, 147.5.
Z-isomer; 15.9, 19.9, 26.4, 26.8, 30.9, 40.4, 111.1, 119.0, 147.2.

(3) FT-IR (neat); cm$^{-1}$: 808, 890, 920, 1379, 1448, 1660, 2249, 2852, 2923.

(4) Odor: (Main Odor) Cumin (Secondary Odor) Smoke, Dry, Wax, Flat, Green, Woody.

(5) Odor Intensity: 4.

Example 3

Production of 4-Cyclohexylpentanenitrile (I-3)

According to the following scheme, 4-cyclohexyl-2-pentenenitrile (I-1) was hydrogenated and thereby 4-cyclohexylpentanenitrile (I-3) was obtained. In Formula (I-1), the bond represented by a wavy line indicates a cis form, a trans form, or a mixture of a cis form and a trans form.

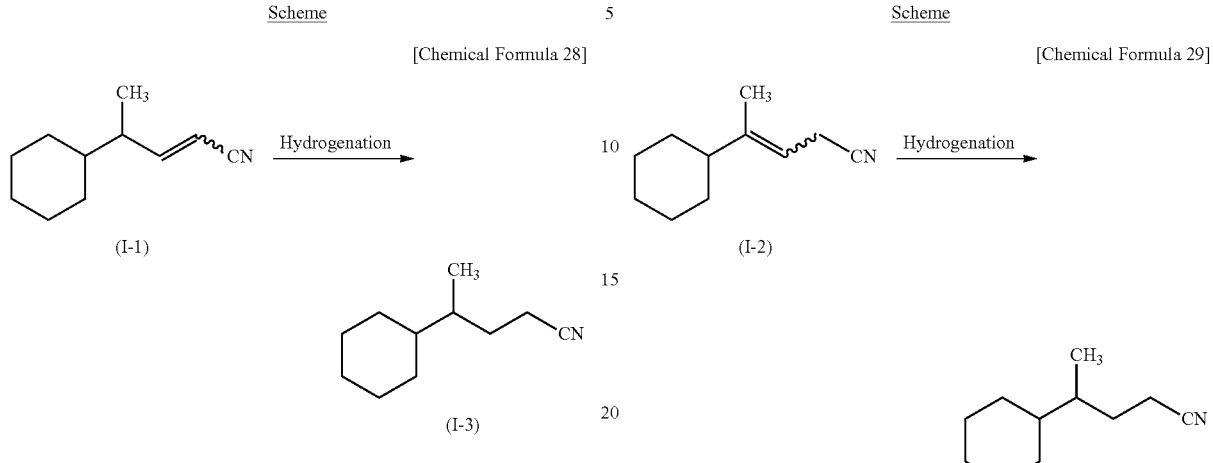

In a 100 mL flask, 1.1 g of the 4-cyclohexyl-2-pentenenitrile (I-1) (with a purity of 99.8% and a pure content of 1.1 g, 6.72 millimoles) that was synthesized in Example 1, 0.02 g of 5% palladium carbon (a 50% by mass water-containing product) (1.8% by mass with respect to the 4-cyclohexyl-2-pentenenitrile (I-1)), and 30 g of methanol (2700% by mass with respect to the 4-cyclohexyl-2-pentenenitrile (I-1)) were placed, which then was stirred under a hydrogen atmosphere of 0.51 MPa at room temperature for 2.5 hours. The reaction mixture was subjected to gas chromatography analysis. As a result, the conversion ratio of the 4-cyclohexyl-2-pentenenitrile (I-1) into 4-cyclohexylpentanenitrile (I-3) was 100% and the reaction yield was 93.1%. The reaction solution obtained after the reaction was completed was filtered and then methanol was distilled. Thereafter, 1.06 g of the concentrated liquid thus obtained was purified by normal phase silica gel column chromatography with a 1 v/v % ethyl acetate/hexane solvent, which then was subjected to Kugelrohr distillation. Thus, 0.88 g of colorless liquid was obtained. The colorless liquid thus obtained was subjected to gas chromatography (GC) analysis. As a result, the 4-cyclohexylpentanenitrile (I-3) had a purity of 100% and an isolated yield of 80.5%.

The measurement results of each spectrum analysis and odor evaluation are indicated below.

(1) $^1$H-NMR (CDCl$_3$, 400 MHz); δ (ppm): 0.85 (3H, d, J=6.4 Hz), 1.01 (2H, m), 1.09 (1H, m), 1.20 (3H, m), 1.44 (2H, m), 1.60 (2H, m), 1.68 (2H, m), 1.74 (3H, m), 2.31 (2H, m).

(2) $^{13}$C-NMR (CDCl$_3$, 100 MHz); δ (ppm): 15.1, 27.0, 27.1, 27.2, 28.9, 30.0, 30.9, 37.6, 42.6, 120.3.

(3) FT-IR (neat); cm$^{-1}$: 891, 1383, 1427, 1448, 2243, 2852, 2924.

(4) Odor: (Main Odor) Cumin (Secondary Odor) Sandalwood, Guaiac, Orris, Green, Celery, Citrus.

(5) Odor Intensity: 4.

Example 4

Production of 4-Cyclohexylpentanenitrile (I-3)

According to the following scheme, 4-cyclohexyl-3-pentenenitrile (I-2) was hydrogenated and thereby 4-cyclohexylpentanenitrile (I-3) was obtained. In Formula (I-2), the bond represented by a wavy line indicates a cis form, a trans form, or a mixture of a cis form and a trans form.

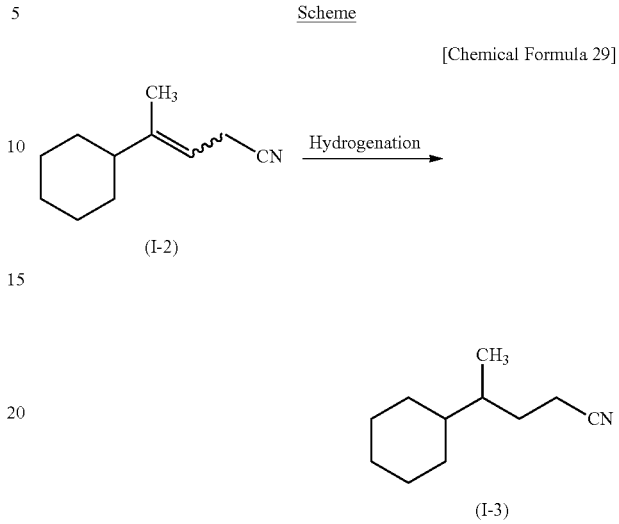

In a 500 mL flask, 40.1 g of the 4-cyclohexyl-3-pentenenitrile (I-2) (with a purity of 97.8% and a pure content of 39.2 g, 0.24 mole) that was synthesized in Example 2, 0.4 g of 5% palladium carbon (a 50% by mass water-containing product) (1.0% by mass with respect to the 4-cyclohexyl-3-pentenenitrile (I-2)), and 40.8 g of isopropanol (98% by mass with respect to the 4-cyclohexyl-3-pentenenitrile (I-2)) were placed, which then was stirred under a hydrogen atmosphere of 0.5 MPa for 71 hours after the temperature thereof was raised to 50° C. Gas chromatography analysis was carried out and as a result, the conversion ratio of the 4-cyclohexyl-3-pentenenitrile (I-2) into 4-cyclohexylpentanenitrile (I-3) was 100% and the reaction yield was 83.3%. The reaction solution obtained after the reaction was completed was filtered and then isopropanol was distilled. Thereafter, 39.8 g of the concentrated liquid thus obtained was subjected to simple distillation and then 28.5 g of main fraction was purified by normal phase silica gel column chromatography with a 1 v/v % ethyl acetate/hexane solvent. Thus, 27.3 g of colorless liquid was obtained. The colorless liquid thus obtained was subjected to gas chromatography (GC) analysis. As a result, the 4-cyclohexylpentanenitrile (I-3) had a purity of 96.1% and an isolated yield of 66.1%.

Example 5

Production of Mixture of 4-Cyclohexyl-2-Pentenenitrile (I-1) and 4-Cyclohexyl-3-Pentenenitrile (I-2): Acetonitrile Method According to the following scheme, 2-cyclohexylpropanal (II) ("Pollenal II" (Trade Name), manufactured by Kao Corporation) and acetonitrile (V) were condensed and thereby a mixture of 4-cyclohexyl-2-pentenenitrile (I-1) and 4-cyclohexyl-3-pentenenitrile (I-2) was obtained. In Formula (I-1) and Formula (I-2), the bond represented by a wavy line indicates a cis form, a trans form, or a mixture of a cis form and a trans form.

Scheme

[Chemical Formula 30]

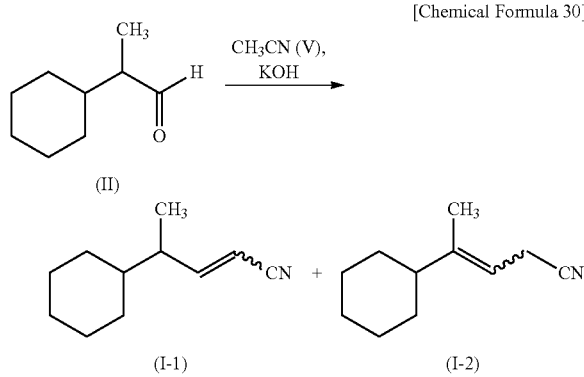

In a 200 mL flask, 7.1 g of granular 85% potassium hydroxide (with a pure content of 6.0 g, 0.11 mole, 1.1 times by mole with respect to the 2-cyclohexylpropanal (II)) and 78 g of acetonitrile (V) (1.9 moles, 19 times by mole with respect to the 2-cyclohexylpropanal (II)) were placed, which then was subjected to nitrogen substitution. Thereafter, this was stirred at 80° C. under reflux for 1.5 hours while stirring and thereby the potassium hydroxide was dissolved, into which 14.0 g (0.10 mole) of the 2-cyclohexylpropanal (II) ("Pollenal II" (Trade Name of Kao)) was dropped at once. This was reacted for ten minutes and then 200 g of granular ice was added thereto to cool it. Dichloroethane was added to the reaction solution, the aqueous layer in the lower layer was extracted by settled separation, and the organic layer was washed with saturated brine. From the aforementioned organic layer, the organic layer in the lower layer was extracted by settled separation. The organic layer thus obtained was dried with sodium sulfate, which then was filtered. Thereafter, the solvent was distilled and thereby a concentrated liquid was obtained. The concentrated liquid thus obtained was subjected to gas chromatography analysis. As a result, the conversion ratio of the 2-cyclohexylpropanal (II) into 4-cyclohexyl-2-pentenenitrile (I-1) and 4-cyclohexyl-3-pentenenitrile (I-2) was 97.6%. In the concentrated liquid obtained above, a total reaction yield of the 4-cyclohexyl-2-pentenenitrile (I-1) and the 4-cyclohexyl-3-pentenenitrile (I-2) was 47.4%. Furthermore, the mass ratio of the 4-cyclohexyl-2-pentenenitrile (I-1) to the 4-cyclohexyl-3-pentenenitrile (I-2) was 45.4/54.6, which was determined from the GC area ratio.

The ratio of isomers of the 4-cyclohexyl-2-pentenenitrile (I-1) was E-isomers:Z-isomers=46:54, which was determined from the GC area ratio, while the ratio of isomers of the 4-cyclohexyl-3-pentenenitrile (I-2) was E-isomers:Z-isomers=81:19, which was determined from the GC area ratio.

Example 6

Production of Mixture of 4-Cyclohexyl-2-Pentenenitrile (I-1) and 4-Cyclohexyl-3-Pentenenitrile (I-2): Isomerization Method According to the following scheme, 4-cyclohexyl-3-pentenenitrile (I-2) was partially isomerized and a mixture of 4-cyclohexyl-3-pentenenitrile (I-2) and 4-cyclohexyl-2-pentenenitrile (I-1) was obtained. In Formula (I-1) and Formula (I-2), the bond represented by a wavy line indicates a cis form, a trans form, or a mixture of a cis form and a trans form.

Scheme

[Chemical Formula 31]

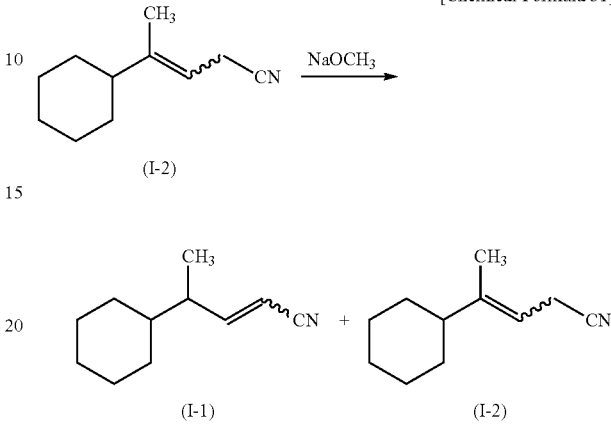

In a 20 mL screw tube, 0.82 g of the 4-cyclohexyl-3-pentenenitrile (I-2) (with a purity of 97.8% and a pure content of 0.80 g, 4.9 millimoles, E-isomers:Z-isomers=75:25) that was synthesized in Example 2 was placed, which then was subjected to nitrogen substitution. Thereafter, 1.00 g of sodium methoxide (a 28% methanol solution) (with a pure content of 0.28 g, 5.2 millimoles, 1.1 times by mole with respect to the 4-cyclohexyl-3-pentenenitrile (I-2)) was dropped thereinto at 25° C. while stirring. This was reacted at 25° C. for 15 hours and thereby a reaction mixture was obtained. The reaction mixture thus obtained was subjected to gas chromatography analysis. As a result, the conversion ratio of the 4-cyclohexyl-3-pentenenitrile (I-2) into 4-cyclohexyl-2-pentenenitrile (I-1) was 56.3% and the total reaction yield of the 4-cyclohexyl-2-pentenenitrile (I-1) and the 4-cyclohexyl-3-pentenenitrile (I-2) was 73.2%. Furthermore, the mass ratio of the 4-cyclohexyl-2-pentenenitrile (I-1) to the 4-cyclohexyl-3-pentenenitrile (I-2) was 40.3/59.7, which was determined from the GC area ratio.

The ratio of isomers of the 4-cyclohexyl-2-pentenenitrile (I-1) was E-isomers:Z-isomers=53:47, which was determined from the GC area ratio, while the ratio of isomers of the 4-cyclohexyl-3-pentenenitrile (I-2) was E-isomers:Z-isomers=79:21, which was determined from the GC area ratio.

Example 7

Production of Mixture of 4-Cyclohexyl-2-Pentenenitrile (I-1) and 4-Cyclohexyl-3-Pentenenitrile (I-2): Isomerization Method According to the following scheme, 4-cyclohexyl-3-pentenenitrile (I-2) was partially isomerized and a mixture of 4-cyclohexyl-3-pentenenitrile (I-2) and 4-cyclohexyl-2-pentenenitrile (I-1) was obtained. In Formula (I-1) and Formula (I-2), the bond represented by a wavy line indicates a cis form, a trans form, or a mixture of a cis form and a trans form.

Scheme

[Chemical Formula 32]

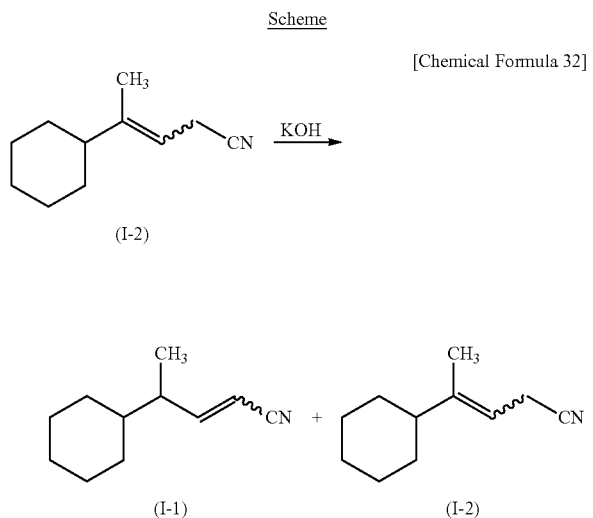

Scheme

[Chemical Formula 33]

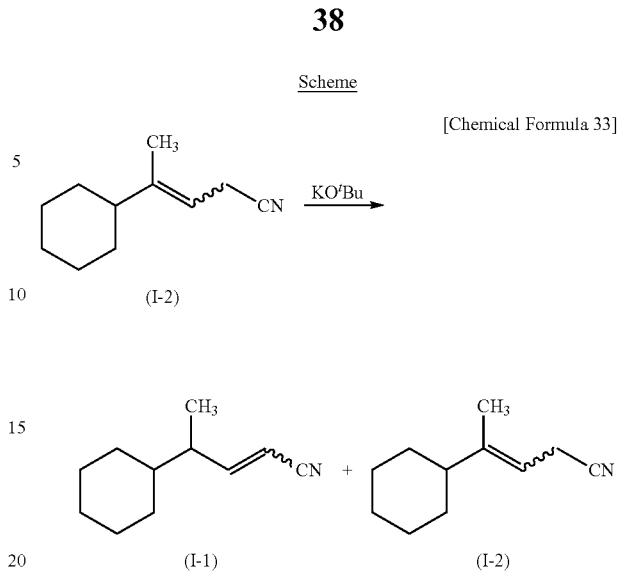

In a 20 mL screw tube, 1.08 g of 85% potassium hydroxide (with a pure content of 0.92 g, 16.4 millimoles, 1.7 times by mole with respect to the 4-cyclohexyl-3-pentenenitrile (I-2)) and 20 g of methanol (0.62 mole, 12 times by mass with respect to the 4-cyclohexyl-3-pentenenitrile (I-2)) were placed, which then was subjected to nitrogen substitution. Thereafter, 1.63 g of the 4-cyclohexyl-3-pentenenitrile (I-2) (with a purity of 97.8% and a pure content of 1.59 g, 9.7 millimoles, E-isomers:Z-isomers=75:25) that was synthesized in Example 2 was dropped thereinto at 25° C. while stirring. This was reacted at 25° C. for 28 hours and thereby a reaction mixture was obtained. The reaction mixture thus obtained was subjected to gas chromatography analysis. As a result, the conversion ratio of the 4-cyclohexyl-3-pentenenitrile (I-2) into 4-cyclohexyl-2-pentenenitrile (I-1) was 38.6% and the total reaction yield of the 4-cyclohexyl-2-pentenenitrile (I-1) and the 4-cyclohexyl-3-pentenenitrile (I-2) was 91.9%. Furthermore, the mass ratio of the 4-cyclohexyl-2-pentenenitrile (I-1) to the 4-cyclohexyl-3-pentenenitrile (I-2) was 33.2/66.8, which was determined from the GC area ratio.

The ratio of isomers of the 4-cyclohexyl-2-pentenenitrile (I-1) was E-isomers:Z-isomers=86:14, which was determined from the GC area ratio, while the ratio of isomers of the 4-cyclohexyl-3-pentenenitrile (I-2) was E-isomers:Z-isomers=79:21, which was determined from the GC area ratio.

Example 8

Production of Mixture of 4-Cyclohexyl-2-Pentenenitrile (I-1) and 4-Cyclohexyl-3-Pentenenitrile (I-2): Isomerization Method According to the following scheme, 4-cyclohexyl-3-pentenenitrile (I-2) was partially isomerized and a mixture of 4-cyclohexyl-3-pentenenitrile (I-2) and 4-cyclohexyl-2-pentenenitrile (I-1) was obtained. In Formula (I-1) and Formula (I-2), the bond represented by a wavy line indicates a cis form, a trans form, or a mixture of a cis form and a trans form.

In a 20 mL screw tube, 0.78 g of potassium tert-butoxide (7.0 millimoles, in an amount of 1.3 times by mole with respect to the 4-cyclohexyl-3-pentenenitrile (I-2)) and 13.2 g of tert-butanol (0.18 mole, in an amount of 15 times by mass with respect to the 4-cyclohexyl-3-pentenenitrile (I-2)) were placed, which then was subjected to nitrogen substitution. Thereafter, 0.89 g of the 4-cyclohexyl-3-pentenenitrile (I-2) (with a purity of 97.8% and a pure content of 0.87 g, 5.3 millimoles, E-isomers:Z-isomers=75:25) that was synthesized in Example 2 was dropped thereinto at 25° C. while stirring. This was reacted at 25° C. for 19 hours and thereby a reaction mixture was obtained. The reaction mixture thus obtained was subjected to gas chromatography analysis and as a result, the conversion ratio of the 4-cyclohexyl-3-pentenenitrile (I-2) into 4-cyclohexyl-2-pentenenitrile (I-1) was 95.1% and the total reaction yield of the 4-cyclohexyl-2-pentenenitrile (I-1) and the 4-cyclohexyl-3-pentenenitrile (I-2) was 8.8%. Furthermore, the mass ratio of the 4-cyclohexyl-2-pentenenitrile (I-1) to the 4-cyclohexyl-3-pentenenitrile (I-2) was 43.8/56.2, which was determined from the GC area ratio.

The ratio of isomers of the 4-cyclohexyl-2-pentenenitrile (I-1) was E-isomers:Z-isomers=39:61, which was determined from the GC area ratio, while the ratio of isomers of the 4-cyclohexyl-3-pentenenitrile (I-2) was E-isomers:Z-isomers=67:33, which was determined from the GC area ratio.

Example 9

Production of 4-Cyclohexylpentanenitrile (I-3)

(a) (Production of Ethyl 2-Cyano-4-Cyclohexyl-penta-2-enoate (VII-1))

According to the following scheme, 2-cyclohexylpropanal (II) ("Pollenal II" (Trade Name), manufactured by Kao Corporation) and ethyl cyanoacetate (VI-1) were condensed and thereby ethyl 2-cyano-4-cyclohexylpenta-2-enoate (VII-1) was obtained. In Formula (VII-1), the bond represented by a wavy line indicates a cis form, a trans form, or a mixture of a cis form and a trans form.

Scheme

[Chemical Formula 34]

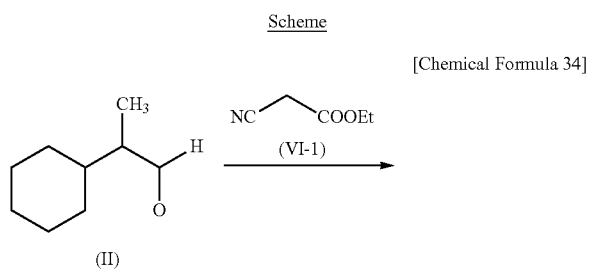

(II) + (VI-1) →

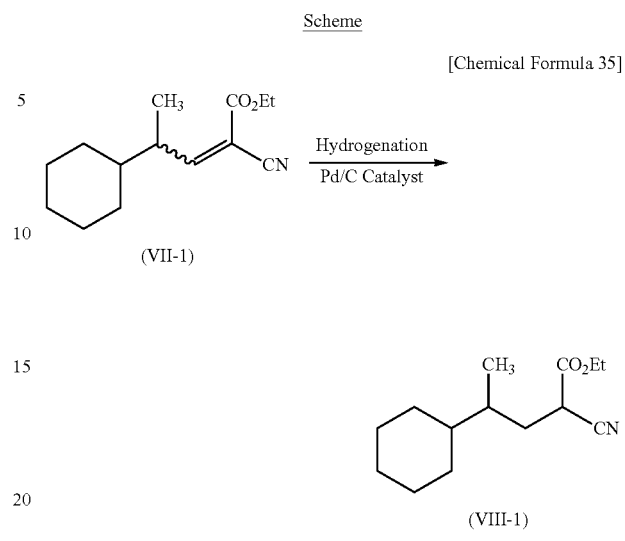

Scheme

[Chemical Formula 35]

(VII-1) → Hydrogenation / Pd/C Catalyst → (VIII-1)

In a 2 L flask with a distillation tube attached thereto, 475 g of ethyl cyanoacetate (VI-1) (4.20 moles, 1.05 times by mole with respect to the 2-cyclohexylpropanal (II)), 6.0 g of acetic acid (0.10 millimole, 0.025 times by mole with respect to the 2-cyclohexylpropanal (II)), and 3.4 g of piperidine (40 millimoles, 0.01 times by mole with respect to the 2-cyclohexylpropanal (II)) were placed, which then was stirred at room temperature. Then, 561 g (4.00 moles) of 2-cyclohexylpropanal (II) ("Pollenal II" (Trade Name), manufactured by Kao Corporation) was dropped thereinto over 40 minutes. Thereafter, this was heated to 50° C., the pressure was reduced gradually to 4.0 kPa over two hours, and the reaction was continued while by-product water was removed. Furthermore, excessive ethyl cyanoacetate was distilled under 130 Pa at 110° C. Then, 921 g of the concentrated liquid thus obtained was subjected to gas chromatography quantitative analysis. As a result, the conversion ratio of the 2-cyclohexylpropanal (II) was 100% and the ethyl 2-cyano-4-cyclohexylpenta-2-enoate (VII-1) had a purity of 98.0% and a reaction yield of 95.9%.

The measurement results of each spectrum analysis are indicated below.

(1) $^1$H-NMR (CDCl$_3$, 400 MHz); δ (ppm): 0.92-1.05 (2H, m), 1.11 (3H, d, J=6.8 Hz), 1.15-1.26 (2H, m), 1.31-1.40 (2H, m), 1.36 (3H, t, J=7.2 Hz), 1.61-1.85 (5H, m), 2.62-2.72 (1H, m), 4.32 (2H, q, J=7.2 Hz), 7.51 (1H, d, J=11.2 Hz).

(2) $^{13}$C-NMR (CDCl$_3$, 100 MHz); δ (ppm): 14.1, 16.6, 26.1, 26.2, 30.3, 30.7, 42.6, 42.7, 62.4, 108.6, 113.9, 161.4, 168.3.

(3) FT-IR (neat); cm$^{-1}$: 764, 1252, 1448, 1624, 1728, 2852, 2925.

(b-1) (Production of Ethyl 2-Cyano-4-Cyclohexylpentanoate (VIII))

According to the following scheme, ethyl 2-cyano-4-cyclohexylpenta-2-enoate (VII-1) was hydrogenated and thereby ethyl 2-cyano-4-cyclohexylpentanoate (VIII) was obtained.

In a 1 L pressure-resistant flask, 480 g of the ethyl 2-cyano-4-cyclohexylpenta-2-enoate (VII-1) (with a purity of 98.0% and a pure content of 471 g, 2.00 moles) that was synthesized in Example 9(a), 9.6 g of 5% palladium carbon (a 50% by mass water-containing product) (2.0% by mass with respect to the ethyl 2-cyano-4-cyclohexylpenta-2-enoate (VII-1)), and 240 g of isopropyl alcohol (50% by mass with respect to the ethyl 2-cyano-4-cyclohexylpenta-2-enoate (VII-1)) were placed, which then was stirred under a hydrogen atmosphere of 0.5 MPa at 50° C. for 20 hours. Then, after the palladium carbon was filtered, isopropanol was distilled. Thereafter, 490 g of the concentrated liquid thus obtained was subjected to gas chromatography analysis. As a result, the conversion ratio of the ethyl 2-cyano-4-cyclohexylpenta-2-enoate (VII-1) was 100% and the ethyl 2-cyano-4-cyclohexylpentanoate (VIII-1) had a purity of 96.5% and a reaction yield of 100%.

The measurement results of each spectrum analysis are indicated below.

(1) $^1$H-NMR (CDCl$_3$, 400 MHz); δ (ppm): 0.90 (6H, d, J=6.8 Hz), 0.98-1.28 (12H, m), 1.32 (3H, t, J=7.2 Hz), 1.33 (3H, t, J=7.2 Hz), 1.52-1.78 (14H, m), 1.96-2.03 (1H, m), 2.04-2.10 (1H, m), 3.47-3.53 (2H, m), 4.26 (4H, q, J=7.2 Hz).

(2) $^{13}$C-NMR (CDCl$_3$, 100 MHz); δ (ppm): 13.9, 15.2, 15.6, 26.50, 26.52, 26.58, 26.64, 26.68, 27.7, 28.7, 30.1, 30.5, 34.3, 34.4, 35.7, 35.8, 36.3, 41.5, 42.8, 62.68, 62.72, 116.5, 116.9, 166.4, 166.7.

(3) FT-IR (neat); cm$^{-1}$: 1186, 1259, 1448, 1743, 2852, 2925.

(b-2) (Production of ethyl 2-cyano-4-cyclohexylpentanoate (VIII-1))

According to the following scheme, ethyl 2-cyano-4-cyclohexylpenta-2-enoate (VII-1) was hydrogenated and thereby ethyl 2-cyano-4-cyclohexylpentanoate was obtained.

Scheme

[Chemical Formula 36]

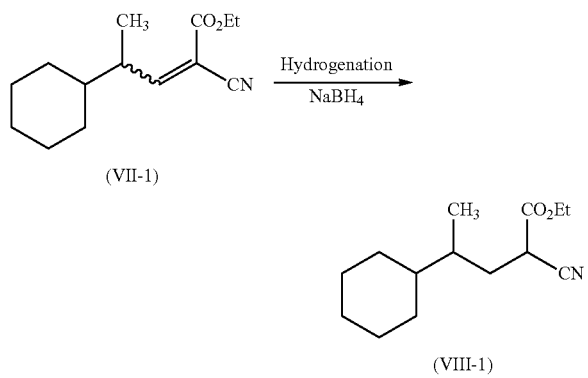

In a 2 L flask, 400 g of the ethyl 2-cyano-4-cyclohexylpenta-2-enoate (with a purity of 98.0% and a pure content of 392 g, 1.67 moles) that was synthesized in Example 9(a) was placed, which then was stirred under a nitrogen atmosphere at 50° C. Then, an aqueous solution composed of 31.6 g of sodium borohydride (0.835 mole, 0.50 times by mole with respect to the ethyl 2-cyano-4-cyclohexylpenta-2-enoate (VII-1)) and 284 g of 0.1M sodium hydroxide aqueous solution was dropped thereinto over two hours while the dropping rate was adjusted so that the internal temperature did not exceed 60° C. Furthermore, this was stirred at 50° C. for 15 minutes until the generation of gas from the system stopped. Thereafter, it was cooled to room temperature and then 480 g of 1M sulfuric acid aqueous solution was dropped thereinto. Then ethyl acetate was added to the reaction solution, the aqueous layer in the lower layer was extracted by settled separation, and the organic layer was washed twice with saturated brine. The organic layer thus obtained was dried with sodium sulfate, which then was filtered. Thereafter, the solvent was distilled and thereby 450 g of concentrated liquid was obtained. This liquid was subjected to gas chromatography analysis. As a result, the conversion ratio of the ethyl 2-cyano-4-cyclohexylpenta-2-enoate (VII-1) was 100% and the ethyl 2-cyano-4-cyclohexylpentanoate (VIII-1) had a purity of 70.3% and a reaction yield of 79.9%.

(c) (Production of 4-Cyclohexylpentanenitrile (I-3))

According to the following scheme, ethyl 2-cyano-4-cyclohexylpentanoate (VIII) was dealkoxycarboxylated and thereby 4-cyclohexylpentanenitrile (I-3) was obtained.

Scheme

[Chemical Formula 37]

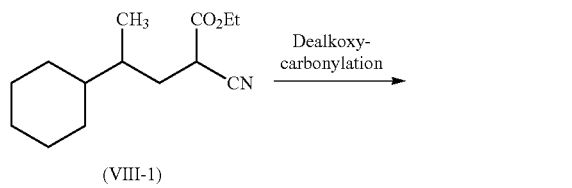

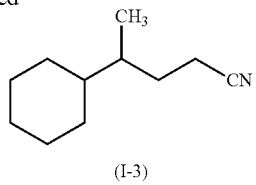

In a 30 mL flask, 1.00 g of the ethyl 2-cyano-4-cyclohexylpentanoate (VIII-1) (with a purity of 98.4% and a pure content of 984 mg, 4.15 millimoles) that was synthesized in Example 9(b-1) or 9(b-2), 0.50 g of potassium acetate (5.1 millimoles, 1.2 times by mole with respect to the ethyl 2-cyano-4-cyclohexylpentanoate (VIII-1)), 1.0 g of N,N-dimethylformamide (100% by mass with respect to the ethyl 2-cyano-4-cyclohexylpentanoate (VIII-1)), and 97 mg of water (5.4 millimoles, 1.3 times by mole with respect to the ethyl 2-cyano-4-cyclohexylpentanoate (VIII-1)) were placed, which then was refluxed in an oil bath at 150° C. for five hours. This reaction solution was subjected to gas chromatography analysis. As a result, the conversion ratio of the ethyl 2-cyano-4-cyclohexylpentanoate (VIII-1) was 100% and the 4-cyclohexylpentanenitrile (I-3) had a reaction yield of 97.1%.

Production of Fragrance Composition, Cleaner Composition, Etc.

Example 10 and Comparative Examples 1 and 2

Floral-Woody Tone Fragrance Composition

Using the 4-cyclohexylpentanenitrile (I-3) obtained in Example 3, a floral-woody tone fragrance composition was prepared in such a manner as to have a composition indicated in Table 1 (Example 10). Furthermore, for comparison, a floral-woody tone fragrance composition in which the 4-cyclohexylpentanenitrile (I-3) was not used (Comparative Example 1) and a floral-woody tone fragrance composition in which Peonile was used instead of the 4-cyclohexylpentanenitrile (I-3) (Comparative Example 2) were prepared.

TABLE 1

| Floral-Woody Tone Fragrance Composition | (Unit: Part by Mass) | | |
|---|---|---|---|
| | Ex. 10 | C. Ex. 1 | C. Ex. 2 |
| Aldehyde C-12 MNA[1] | 3 | 3 | 3 |
| Allyl Amyl Glycolate[2] | 2 | 2 | 2 |
| Ambroxan[3] | 0.5 | 0.5 | 0.5 |
| Bacdanol[4] | 20 | 20 | 20 |
| Benzyl Acetate | 15 | 15 | 15 |
| cis-3-Hexenol | 1 | 1 | 1 |
| Citronellol | 30 | 30 | 30 |
| δ-Damascone | 3 | 3 | 3 |
| Dihydromyrcenol | 30 | 30 | 30 |
| Ethyl Acetate | 2 | 2 | 2 |
| Ethyl Acetoacetate | 2 | 2 | 2 |
| Ethyllinalool | 20 | 20 | 20 |
| Fruitate[5] | 5 | 5 | |
| γ-Terpinene | 5 | 5 | 5 |
| Habanolide[6] | 30 | 30 | 30 |
| Heliotropine | 5 | 5 | 5 |
| Hexyl Acetate | 1 | 1 | 1 |
| Hexyl Cinnamic Aldehyde[7] | 200 | 200 | 200 |
| Irotyl[8] | 4 | 4 | 4 |
| Iso E Super[9] | 100 | 100 | 100 |
| Lemon Oil California | 10 | 10 | 10 |
| Liffarome[10] | 1.5 | 1.5 | 1.5 |
| Triplal[11] | 2 | 2 | 2 |

TABLE 1-continued

| Floral-Woody Tone Fragrance Composition | (Unit: Part by Mass) | | |
|---|---|---|---|
| | Ex. 10 | C. Ex. 1 | C. Ex. 2 |
| Lilyall[12] | 30 | 30 | 30 |
| Linalyl Acetate | 20 | 20 | 20 |
| Methyl Benzoate | 1 | 1 | 1 |
| γ-Methylionone | 30 | 30 | 30 |
| Patchouli Oil | 0.5 | 0.5 | 0.5 |
| Phenylethyl Alcohol | 30 | 30 | 30 |
| 2-Phenylethyl Methyl Ether | 0.5 | 0.5 | 0.5 |
| Rose Oxide | 1 | 1 | 1 |
| Tetrahydrolinalool | 40 | 40 | 40 |
| Vanillin | 5 | 5 | 5 |
| Peonile[13] | 0 | 0 | 13 |
| 4-Cyclohexylpentanenitrile (I-3) | 3 | 0 | 0 |
| Dipropylene Glycol | 347 | 350 | 337 |
| Total | 1000 | 1000 | 1000 |

[1] Trade Name of Kao, 2-Methyl-undecanal
[2] Trade Name of IFF, Allyl 2-pentyloxy acetate
[3] Trade Name of Kao, [3aR-(3a.α,5a.β,9a.α,9b.β)]Dodecahydro-3a,6,6,9a-tetramethyl-naphtho[2,1-b]furan
[4] Trade Name of IFF, (2-Ethyl-4-(2,2,3-trimethyl-3-cyclopenten-1-yl)-2-buten-1-ol
[5] Trade Name of Kao, Ethyl tricyclo [5.2.1.0$^{2.6}$] decan-2 carboxylate
[6] Trade Name of Firmenich, Oxacyclohexadec-12(11)-en-2-one
[7] Trade Name of Kao, 2-n-Hexyl-3-phenyl-2-propenal
[8] Trade Name of Kao, Ethyl 2-ethyl capronate
[9] Trade Name of IFF, 1-(1,2,3,4,5,6,7,8-Octahydro-2,3,8,8-tetramethyl-2-naphthalenyl)-ethan-1-one
[10] Trade Name of IFF, cis-3-Hexenyl methyl carbonate
[11] Trade Name of IFF, 2,4-Dimethyl-3-cyclohexane-1-carboxaldehyde
[12] Trade Name of Givaudan, p-tert-Butyl-alpha-methylhydrocinnamic aldehyde
[13] Trade Name of Givaudan, 2-Cyclohexylidene-2-phenylacetonitrile The evaluations of the floral-woody tone fragrance compositions of Example 10 as well as Comparative Examples 1 and 2 were performed in the same manner as in the aforementioned odor evaluation. As compared to the floral-woody tone fragrance compositions of Comparative Examples 1 and 2, the floral-woody tone fragrance composition of Example 10 not only had a stronger woody tone but also became sweeter, milder, and more harmonious. Moreover, the floral-woody tone fragrance composition of Example 10 had a further reinforced intensity of the fragrance, resulting in an increased presence. As compared to the fragrance composition of Comparative Example 2 in which Peonile was further added, in the floral-woody tone fragrance composition of Example 10, an undesirable metallic tone was concealed very well and thereby a desirable floral tone was enhanced.

Example 11 and Comparative Examples 3 and 4

Liquid Cleaner for Clothing

To a non-fragranced liquid cleaner for clothing having the composition indicated in Table 2, each of the floral-woody tone fragrance compositions obtained in Example 10 and Comparative Examples 1 and 2 was added in such a manner as to be contained in an amount of 0.4% by mass. Thus, liquid cleaners for clothing of Example 11 and Comparative Examples 3 and 4 were prepared, respectively.

TABLE 2

| Non-Fragranced Liquid Cleaner For Clothing | Blended Amount (% by mass) |
|---|---|
| Sodium Polyoxyethylene(2)Lauryl Ether Sulfate[1] | 9.1 |
| Polyethoxyethylenated Alcohol[2] | 6.4 |
| Linear Fatty Acid[3] | 2.9 |
| Citric Acid | 3.0 |

TABLE 2-continued

| Non-Fragranced Liquid Cleaner For Clothing | Blended Amount (% by mass) |
|---|---|
| 50% Sodium Hydroxide | 2.8 |
| Ethanol | 1.0 |
| Preservative[4] | 0.15 |
| Sodium Chloride | Suitable Amount |
| Ion Exchanged Water | Remainder |
| pH | 8.3 |

[1] Trade Name of Kao: Emal 270E
[2] Trade Name of Kao: Findet 1315/19CP
[3] Trade Name of Uniqema: Prifac 7901
[4] Trade Name of Lamirsa: Mirecide NB/70

The evaluations of the liquid cleaners for clothing of Example 11 and Comparative Examples 3 and 4 were performed as follows. Two experts who had an experience of at least five years but less than ten years as well as two experts who had an experience of at least 25 years of blending odors and evaluating fragrances determined the preference, intensity, and overall evaluation of the odor at the mouth of the bottle. The preference was indicated by the relative evaluation, with 0 denoting a very unpleasant odor and 5 denoting a very preferable odor. The odor intensity was indicated by the relative evaluation, with 0 denoting odorless and 5 denoting very strong. The overall evaluation was indicated by the relative evaluation based on the preference and the intensity, with 0 denoting a very bad odor and 5 denoting a very good odor. The results are indicated in Table 3.

TABLE 3

| Liquid Cleaner For Clothing - Fragrance Evaluation | Ex. 11 | C. Ex. 3 | C. Ex. 4 |
|---|---|---|---|
| Preference | 4.3 | 4.0 | 4.1 |
| Intensity | 4.3 | 4.0 | 4.0 |
| Overall Evaluation | 4.4 | 4.2 | 4.2 |

As compared to the liquid cleaner for clothing of Comparative Example 3, the liquid cleaner for clothing of Example 11 not only had an enhanced woody tone but also became sweeter, milder, and more harmonious, resulting in an increased preference. Moreover, the liquid cleaner for clothing of Example 11 had a further enhanced intensity of the fragrance, resulting in an increased presence. As compared to the fragrance composition of Comparative Example 4 in which Peonile was further added, in the liquid cleaner for clothing of Example 11, an undesirable metallic tone was concealed very well and thereby a desirable floral tone was enhanced.

Example 12 and Comparative Example 5

Green-Floral (Magnolia) Tone Fragrance Composition

Using the 4-cyclohexylpentanenitrile (I-3) obtained in Example 3, a green-floral (magnolia) tone fragrance composition was prepared in such a manner as to have a composition indicated in Table 4 (Example 12). Furthermore, for comparison, a green-floral (magnolia) tone fragrance composition was prepared without using the 4-cyclohexylpentanenitrile (I-3) (Comparative Example 5).

TABLE 4

| Green·Floral (Magnolia) Tone Fragrance Composition | Ex. 12 | C. Ex. 5 |
|---|---|---|
| | (Unit: Part by Mass) | |
| 2,6-Nonadienal | 0.5 | 0.5 |
| Acetaldehyde Ethyl Linalyl Acetal | 5 | 5 |
| α-Damascone | 1.5 | 1.5 |
| Canthoxal[1] | 10 | 10 |
| Citronellol | 75 | 75 |
| Cyclamen Aldehyde | 50 | 50 |
| Floralozone[2] | 15 | 15 |
| Geraniol | 25 | 25 |
| Helional[3] | 15 | 15 |
| Jasmacyclat[4] | 50 | 50 |
| MDJ[5] | 250 | 250 |
| Terpineol | 75 | 75 |
| Tetrahydrolinalool | 100 | 100 |
| Undecavertol[6] | 10 | 10 |
| 4-Cyclohexylpentanenitrile (I-3) | 2.5 | 0 |
| Dipropylene Glycol | 315.5 | 318 |
| Total | 1000 | 1000 |

[1] Trade Name of IFF, 2-Methyl-3-(p-methoxyphenyl)propanal
[2] Trade Name of IFF, p-Ethyl-2,2-dimethyl-hydrocinnamicaldehyde
[3] Trade Name of IFF, 2-Methyl-3-(3,4-methylenedioxyphenyl)propanal
[4] Trade Name of Kao, Methyl cyclooctyl carbonate
[5] Trade Name of Kao, Methyl dihydrojasmonate
[6] Trade Name of Givaudan, 4-Methyl-3-decen-5-ol The evaluations of the green-floral (magnolia) tone fragrance compositions of Example 12 and Comparative Example 5 were performed in the same manner as in the aforementioned odor evaluation. As compared to the green-floral (magnolia) tone fragrance composition of Comparative Example 6, in the green-floral (magnolia) tone fragrance composition of Example 12, not only the woody tone was enhanced but also a green tone odor was provided, resulting in enhanced freshness and naturalness, which further completed a magnolia feeling. Moreover, in the green-floral (magnolia) tone fragrance composition of Example 12, a preferable floral tone was enhanced and the diffusibility of the fragrance was further increased.

Example 13 and Comparative Example 6

Hair Cleaner (Shampoo)

The green-floral (magnolia) tone fragrance compositions obtained in Example 12 and Comparative Example 5 each was added to a non-fragranced hair cleaner having the composition indicated in Table 5 in such a manner as to be contained in an amount of 0.5% by mass and thus, hair cleaners of Example 13 and Comparative Example 6 were prepared, respectively.

TABLE 5

| Non-Fragranced Hair Cleaner (Shampoo) | Blended Amount (% by mass) |
|---|---|
| Sodium Polyoxyethylene(2)Lauryl Ether Sulfate[1] | 14.7 |
| Cocamide Propyl Betaine[2] | 10.0 |
| Cocamide Diethanol Amide[3] | 1.5 |
| Sodium Chloride | 0.3 |
| Preservative[4] | 0.1 |
| 20% Citric Acid | Suitable Amount |
| 0.1% Sodium Hydroxide | Suitable Amount |
| Ion Exchanged Water | Remainder |
| pH | 6 |

[1] Trade Name of Kao: Emal 227
[2] Trade Name of Kao: Betadet HR
[3] Trade Name of Kao: Amidet B-112
[4] Trade Name of Lonza: Isocil PC The evaluations of the hair cleaners of Example 13 and Comparative Example 6 were performed as follows. Two experts who had an experience of at least five years but less than ten years as well as two experts who had an experience of at least 25 years of blending odors and evaluating fragrances determined the fragrance note of the odor at the mouth of the bottle.

As compared to the hair cleaner of Comparative Example 6, in the hair cleaner of Example 13, not only the woody tone was enhanced but also a green tone odor was provided, resulting in enhanced freshness and naturalness, which further completed a magnolia feeling. Moreover, in the hair cleaner of Example 13, a preferable floral tone was enhanced and the diffusibility of the fragrance was further increased.

Example 14 and Comparative Example 7

Pine Tone Fragrance Composition

Using the 4-cyclohexylpentanenitrile (I-3) obtained in Example 3, a pine tone fragrance composition was prepared in such a manner as to have a composition indicated in Table 6 (Example 14). Furthermore, for comparison, a pine tone fragrance composition was prepared without using the 4-cyclohexylpentanenitrile (I-3) (Comparative Example 7).

TABLE 6

| Pine Tone Fragrance Composition | Ex. 14 | C. Ex. 7 |
|---|---|---|
| | (Unit: Part by Mass) | |
| Aldehyde C-12 MNA[1] | 10 | 10 |
| Aldehyde C-16[2] | 0.5 | 0.5 |
| α-Pinene | 80 | 80 |
| Benzyl Acetate | 30 | 30 |
| β-Pinene | 30 | 30 |
| Camphene | 10 | 10 |
| Cedar Wood Oil, Virginia | 10 | 10 |
| Ethyl Heptanoate | 5 | 5 |
| Ethyl Maltol | 0.05 | 0.05 |
| Eucalyptus Oil | 20 | 20 |
| Eugenol | 3 | 3 |
| Fenchyl Alcohol | 5 | 5 |
| Isobornyl Acetate | 300 | 300 |
| Lavender Oil, M.B 40/42 | 10 | 10 |
| Lime Oil | 10 | 10 |
| Raspberry Ketone | 5 | 5 |
| Terpinyl Acetate | 30 | 30 |
| 4-Cyclohexylpentanenitrile (I-3) | 10 | 0 |
| Dipropylene Glycol | 431.45 | 441.45 |
| Total | 1000 | 1000 |

[1] Trade Name of Kao, 2-Methyl undecanal
[2] Common Name, Ethyl 3-methyl-3-phenyl glycidate The evaluations of the pine tone fragrance compositions of Example 14 and Comparative Example 7 were performed in the same manner as in the aforementioned odor evaluation. As compared to the pine tone fragrance composition of Comparative Example 7, in the pine tone fragrance composition of Example 14, the green feeling and the herbal feeling of the pine tone were enhanced and the diffusibility of the fragrance also was increased. In the pine tone fragrance composition of Example 14, the green sweetness of the pine tone was enhanced and thereby a sense of naturalness was obtained. In the pine tone fragrance composition of Example 14, not only the intensity of the fragrance also was enhanced but also the 4-cyclohexylpentanenitrile (I-3) emphasized the component forming the woody tone.

Example 15 and Comparative Example 8

All Purpose Cleaner

The pine tone fragrance compositions obtained in Example 14 and Comparative Example 7 each were added to a non-fragranced all purpose cleaner having a composition indicated in Table 7 in such a manner as to be contained in an amount of 0.5% by mass, and thereby all purpose cleaners of Example 15 and Comparative Example 8 were prepared, respectively.

TABLE 7

| Non-Fragranced All Purpose Cleaner (APC) | Blended Amount (% by mass) |
|---|---|
| Polyethoxyethylenated C14-15 Branched Alcohol[1] | 8.1 |
| Hydrogenated Castor Oil[2] | 1.7 |
| Benzalkonium Chloride[3] | 0.5 |
| Preservative[4] | 0.05 |
| Ion Exchanged Water | Remainder |
| pH | 5.4 |

[1]Trade Name of Kao: Findet LR4/2585
[2]Trade Name of Kao: Findet ARH/52
[3]Trade Name of Kao: Tetranyl BC-80
[4]Trade Name of Thor Specialities: Acticide SPX The evaluations of the all purpose cleaners of Example 15 and Comparative Example 8 were performed as follows. One expert who had an experience of at least five years but less than ten years as well as two experts who had an experience of at least 25 years of blending odors and evaluating fragrances determined the fragrance note of the odor at the mouth of the bottle.

As compared to the all purpose cleaner of Comparative Example 8, in the all purpose cleaner of Example 15, the green feeling and the herbal feeling of the pine tone were enhanced and the diffusibility of the fragrance also was increased. In the all purpose cleaner of Example 15, the green sweetness of the pine tone was enhanced and thereby a sense of naturalness was obtained. In the all purpose cleaner of Example 15, not only the intensity of the fragrance also was enhanced but also the 4-cyclohexylpentanenitrile (I-3) emphasized the component forming the woody tone.

Example 16 and Comparative Example 9

Basil Tone Fragrance Composition

Using the 4-cyclohexylpentanenitrile (I-3) obtained in Example 3, a basil tone fragrance composition was prepared in such a manner as to have a composition indicated in Table 8 (Example 16). Furthermore, for comparison, a basil tone fragrance composition was prepared without using the 4-cyclohexylpentanenitrile (I-3) (Comparative Example 9).

TABLE 8

| Basil Tone Fragrance Composition | Ex. 16 | C. Ex. 9 |
|---|---|---|
| | (Unit: Part by Mass) | |
| Anethole | 5 | 5 |
| Basil Oil | 50 | 50 |
| Camphor | 3 | 3 |
| Cedar Wood Oil, Virginia | 5 | 5 |
| cis-3-Hexenol | 0.2 | 0.2 |
| Eucalyptus Oil | 10 | 10 |
| Eugenol | 5 | 5 |
| Isobornyl Acetate | 10 | 10 |
| Limonene | 30 | 30 |
| Linalool | 20 | 20 |
| Rosemary Oil | 10 | 10 |
| Terpineol | 10 | 10 |
| Tricyclodecenyl Propionate | 30 | 30 |
| 4-Cyclohexylpentanenitrile (I-3) | 5 | 0 |
| Dipropylene Glycol | 806.8 | 811.8 |
| Total | 1000 | 1000 |

The evaluations of the basil tone fragrance compositions of Example 16 and Comparative Example 9 were performed in the same manner as in the aforementioned odor evaluation. As compared to the basil tone fragrance composition of Comparative Example 9, in the basil tone fragrance composition of Example 16, not only the woody tone was enhanced but also a green feeling and a spicy feeling of the basil were enhanced, which allowed the basil tone to be further effected. In the basil tone fragrance composition of Example 16, the 4-cyclohexylpentanenitrile (I-3) substantially emphasized the component forming a spicy tone.

Example 17 and Comparative Example 10

Concentrated all Purpose Cleaner

The basil tone fragrance compositions obtained in Example 16 and Comparative Example 9 each were added to a non-fragranced concentrated all purpose cleaner having the composition indicated in Table 9 in such a manner as to be contained in an amount of 0.5% by mass, and thereby concentrated all purpose cleaners of Example 17 and Comparative Example 10 were prepared, respectively.

TABLE 9

| Non-Fragranced Concentrated All Purpose Cleaner (APC) | Blended Amount (% by mass) |
|---|---|
| Polyethoxyethylenated Branched C14, C15 Alcohol[1] | 19.5 |
| Hydrogenated Castor Oil[2] | 4.0 |
| Benzalkonium Chloride[3] | 1.25 |
| Preservative[4] | 0.12 |
| Ion Exchanged Water | Remainder |
| pH | 5.8 |

[1]Trade Name of Kao: Findet LR4/2585
[2]Trade Name of Kao: Findet ARH/52
[3]Trade Name of Kao: Tetranyl BC-80
[4]Trade Name of Thor Specialities: Acticide SPX The evaluations of the concentrated all purpose cleaners of Example 17 and Comparative Example 10 were performed as follows. Two experts who had an experience of at least five years but less than ten years as well as two experts who had an experience of at least 25 years of blending odors and evaluating fragrances determined the fragrance note of the odor at the mouth of the bottle.

As compared to the concentrated all purpose cleaner of Comparative Example 10, in the concentrated all purpose cleaner of Example 17, not only the woody tone was enhanced but also a green feeling and a spicy feeling of the basil were enhanced, which allows the basil tone to be further effected. In the concentrated all purpose cleaner of Example 17, the 4-cyclohexylpentanenitrile (I-3) substantially emphasized the component forming a spicy tone.

Examples 18 to 20 and Comparative Examples 11 to 12

Citrus (Orange) Tone Fragrance Composition

Using the 4-cyclohexyl-2-pentenenitrile (I-1) obtained in Example 1, the 4-cyclohexyl-3-pentenenitrile (I-2) obtained in Example 2, and the 4-cyclohexylpentanenitrile (I-3) obtained in Example 3, citrus (orange) tone fragrance compositions were prepared in such a manner as to have compositions indicated in Table 10 (Examples 18, 19, and 20, respectively). Furthermore, for comparison, a citrus (orange) tone fragrance composition in which cuminyl nitrile having a cumin-like odor was used instead of the 4-cyclohexyl-2-pentenenitrile (I-1), the 4-cyclohexyl-3-pentenenitrile (I-2), or the 4-cyclohexylpentanenitrile (I-3) (Comparative Example 11), and a citrus (orange) tone fragrance composition in which the 4-cyclohexyl-2-pentenenitrile (I-1), the 4-cyclohexyl-3-pentenenitrile (I-2), or the 4-cyclohexylpentanenitrile (I-3) was not used (Comparative Example 12) were prepared.

The evaluations of the citrus (orange) tone fragrance compositions of Examples 18 to 20 and Comparative Examples 11 and 12 were performed in the same manner as in the aforementioned odor evaluation. As compared to the citrus (orange) tone fragrance compositions of Comparative Examples 11 and 12, in the citrus (orange) tone fragrance compositions of Examples 18 to 20, the sweetness of orange was emphasized, freshness was enhanced, and at the same time, the diffusibility also was improved. Furthermore, the citrus (orange) tone fragrance compositions of Examples 18 to 20 each provided an effect of reducing the oily feeling of aliphatic aldehyde and had a fresher fragrance. As compared to the citrus (orange) tone fragrance composition of Comparative Example 11, in the citrus (orange) tone fragrance compositions of Examples 18 to 20, an undesirable chemical odor of aliphatic aldehyde was concealed very well and thereby a desirable citrus tone was enhanced. Particularly, the effect of enhancing the citrus tone was most remarkable in the fragrance composition of Example 20. On the other hand, as compared to the citrus (orange) tone fragrance composition of Comparative Example 12, the citrus (orange) tone fragrance composition of Comparative Example 11 had a too strong spicy feeling that resulted in an imbalance in fragrance note and thereby it did not have a citrus odor but a spicy-like fragrance note. As compared to the citrus (orange) tone fragrance composition of Comparative Example 11, the citrus (orange) tone fragrance composition of Comparative Example 12 had a stronger chemical odor

TABLE 10

| Citrus (Orange) Tone Fragrance Composition | Ex. 18 | Ex. 19 | Ex. 20 | C. Ex. 11 | C. Ex. 12 |
|---|---|---|---|---|---|
| Aldehyde C-10[1] | 100 | 100 | 100 | 100 | 100 |
| Aldehyde C-11 MOA[2] | 5 | 5 | 5 | 5 | 5 |
| Aldehyde C-111 LEN | 35 | 35 | 35 | 35 | 35 |
| Aldehyde C-12 MNA[4] | 10 | 10 | 10 | 10 | 10 |
| Aldehyde C-12 LAUR | 20 | 20 | 20 | 20 | 20 |
| Aldehyde C-8[6] | 12 | 12 | 12 | 12 | 12 |
| Aldehyde C-9[7] | 3 | 3 | 3 | 3 | 3 |
| Citral | 25 | 25 | 25 | 25 | 25 |
| Citronellal | 5 | 5 | 5 | 5 | 5 |
| Citronellyl Nitrile | 75 | 75 | 75 | 75 | 75 |
| Cuminaldehyde | 2 | 2 | 2 | 2 | 2 |
| Limonene | 250 | 250 | 250 | 250 | 250 |
| Geraniol | 10 | 10 | 10 | 10 | 10 |
| Triplal[8] | 15 | 15 | 15 | 15 | 15 |
| Manzanate[9] | 8 | 8 | 8 | 8 | 8 |
| Myrcene | 15 | 15 | 15 | 15 | 15 |
| Orange Oil, Pera BM | 150 | 150 | 150 | 150 | 150 |
| trans-2-Hexenal | 1 | 1 | 1 | 1 | 1 |
| 4-Cyclohexyl-2-Pentenenitrile (I-1) | 15 | 0 | 0 | 0 | 0 |
| 4-Cyclohexyl-3-Pentenenitrile (I-2) | 0 | 15 | 0 | 0 | 0 |
| 4-Cyclohexylpentanenitrile (I-3) | 0 | 0 | 15 | 0 | 0 |
| Cuminyl Nitrile | 0 | 0 | 0 | 15 | 0 |
| Dipropylene Glycol | 244 | 244 | 244 | 244 | 259 |
| Total | 1000 | 1000 | 1000 | 1000 | 1000 |

(Unit: Part by Mass)

[1]Trade Name of Kao, 1-Decanal
[2]Trade Name of Symrise, 2-Methyl decanal
[3]Trade Name of Kao, 10-Undecenal
[4]Trade Name of Kao, 2-Methyl undecanal
[5]Trade Name of Kao, 1-Dodecanal
[6]Trade Name of Kao, 1-Octanal
[7]Trade Name of Kao, 1-Nonanal
[8]Trade Name of IFF, 2,4-Dimethyl-3-cyclohexane-1-carboxaldehyde
[9]Trade Name of Givaudan, Ethyl 2-methyl pentanoate and an enhanced pungent odor. Results of the evaluations are shown together in Table 11 below.

TABLE 11

|  | Ex. 18 | Ex. 19 | Ex. 20 | C. Ex. 11 | C. Ex. 12 |
|---|---|---|---|---|---|
| Odor Intensity of Citrus Fragrance (Six Grades) | 4 | 4 | 5 | 1 | 3 |
| Main Odor | Intense citrus | Intense citrus | Very intense citrus | spicy | Weak citrus |
| Secondary Odor | Very weak chemical | Very weak chemical |  | Very weak citrus Very intense chemical | chemical |
| Others | Sweet | Sweet | Sweet, natural, fresh | pungent |  |

Example 21 and Comparative Example 13

Dish Cleaner

The citrus (orange) tone fragrance compositions obtained in Example 20 and Comparative Example 12 were added to a non-fragranced dish cleaner having the composition indicated in Table 12 in such a manner as to be contained in an amount of 0.3% by mass, and thereby dish cleaners of Example 21 and Comparative Example 13 were prepared, respectively.

TABLE 12

| Non-Fragranced Dish Cleaner | Blended Amount (mass %) |
|---|---|
| Sodium Polyoxyethylene(2)Lauryl Ether Sulfate[1] | 44.4 |
| Cocamidopropylamine Oxide[2] | 18.2 |
| Polyoxyethylenated C8-10 Glycerides[3] | 2.0 |
| 50% Citric Acid | 0.50 |
| Sodium Chloride | 0.75 |
| Ion Exchanged Water | Remainder |
| pH | 7.1 |

[1]Trade Name of Kao: Emal 227
[2]Trade Name of Kao: Oxidet L-75 CP
[3]Trade Name of Kao: Levenol N-661

The evaluations of the dish cleaners of Example 21 and Comparative Example 13 were performed as follows. One expert who had an experience of at least five years but less than ten years as well as two experts who had an experience of at least 25 years of blending odors and evaluating fragrances determined the fragrance note of the odor at the mouth of the bottle.

As compared to the dish cleaner of Comparative Example 13, in the dish cleaner of Example 21, the sweetness of orange is emphasized, freshness is enhanced, and at the same time, the diffusibility also is improved. Furthermore, in the dish cleaner of Example 21, an effect of reducing the oily feeling of aliphatic aldehyde is obtained, which results in a fresher fragrance. As compared to the dish cleaner of Comparative Example 13, in the dish cleaner of Example 21, an undesirable chemical odor of aliphatic aldehyde is concealed very well and thereby a desirable citrus tone is enhanced.

Example 22 and Comparative Example 14

Citrus (Grapefruit) Tone Fragrance Composition

Using the 4-cyclohexylpentanenitrile (I-3) obtained in Example 3, a citrus (grapefruit) tone fragrance composition was prepared in such a manner as to have a composition indicated in Table 13 (Example 22). Furthermore, for comparison, a citrus (grapefruit) tone fragrance composition was prepared without using the 4-cyclohexylpentanenitrile (I-3) (Comparative Example 14).

TABLE 13

| Citrus (Grapefruit) Tone Fragrance Composition | (Unit: Part by Mass) | |
|---|---|---|
|  | Ex. 22 | C. Ex. 14 |
| Aldehyde C-10[1] | 10 | 10 |
| Aldehyde C-8[2] | 10 | 10 |
| Allyl Caproate | 2 | 2 |
| Ambrotech[3] | 0.3 | 0.3 |
| cis-3-Hexenol | 2 | 2 |
| Citral | 20 | 20 |
| Citronellol | 20 | 20 |
| Floropal[4] | 10 | 10 |
| Geranium Oil | 1 | 1 |
| Geranyl Acetate | 10 | 10 |
| γ-Undecalactone[5] | 1 | 1 |
| Lemon Oil, Italy | 30 | 30 |
| Linalool | 50 | 50 |
| MDJ[6] | 30 | 30 |
| Orange Oil, Valencia | 420 | 420 |
| Spearmint Oil, MWS | 1 | 1 |
| 4-Cyclohexylpentanenitrile (I-3) | 5 | 0 |
| Dipropylene Glycol | 377.7 | 382.7 |
| Total | 1000 | 1000 |

[1]Trade Name of Kao, 1-Decanal
[2]Trade Name of Kao, 1-Octanal
[3]Trade Name of Kao, Dodecahydro-3a,6,6,9a-tetramethylnaphtho[2,1-b]furan
[4]Trade Name of Symrise, 2,4,6-Trimethyl-2-phenyl-1,3-dioxane
[5]Trade Name of Kao, γ-Undecalactone
[6]Trade Name of Kao, Methyl dihydrojasmonate The evaluations of the citrus (grapefruit) tone fragrance compositions of Example 22 and Comparative Example 14 were performed in the same manner as in the aforementioned odor evaluation. As compared to the citrus (grapefruit) tone fragrance composition of Comparative Example 14, in the citrus (grapefruit) tone fragrance composition of Example 22, the sweetness of grapefruit was emphasized, freshness was enhanced, and at the same time, the diffusibility also was improved. Furthermore, in the citrus (grapefruit) tone fragrance composition of Example 22, an effect of providing a green feeling and a spicy feeling of grapefruit also was obtained, which resulted in a fresher fragrance. As compared to the citrus (grapefruit) tone fragrance composition of Comparative Example 14, in the citrus (grapefruit) tone fragrance composition of Example 22, an undesirable chemical odor of aliphatic aldehyde was concealed very well and thereby a desirable citrus tone was enhanced.

Example 23 and Comparative Example 15

Dish Cleaner

The citrus (grapefruit) tone fragrance compositions obtained in Example 22 and Comparative Example 14 each were added to the non-fragranced dish cleaner indicated in Table 12 in such a manner as to be contained in an amount of 0.5% by mass, and thereby dish cleaners of Example 23 and Comparative Example 15 were prepared, respectively.

The evaluations of the dish cleaners of Example 23 and Comparative Example 15 were performed as follows. One expert who had an experience of at least five years but less than ten years as well as two experts who had an experience of at least 25 years of blending odors and evaluating fragrances determined the fragrance note of the odor at the mouth of the bottle.

As compared to the dish cleaner of Comparative Example 15, in the dish cleaner of Example 23, the sweetness of grapefruit was emphasized, freshness was enhanced, and at the same time, the diffusibility also was improved. Furthermore, in the dish cleaner of Example 23, an effect of providing a green feeling and a spicy feeling of grapefruit also was obtained, which resulted in a fresher fragrance. As compared to the dish cleaner of Comparative Example 15, in the dish cleaner of Example 23, an undesirable chemical odor of aliphatic aldehyde was concealed very well and thereby a desirable citrus tone was enhanced.

Example 24 and Comparative Example 16

Floral (Muguet) Tone Fragrance Composition

Using the 4-cyclohexylpentanenitrile (I-3) obtained in Example 3, a floral (muguet) tone fragrance composition was prepared in such a manner as to have a composition indicated in Table 14 (Example 24). Furthermore, for comparison, a floral (muguet) tone fragrance composition was prepared without using the 4-cyclohexylpentanenitrile (I-3) (Comparative Example 16).

TABLE 14

| Floral (Muguet) Tone Fragrance Composition | Ex. 24 | (Unit: Part by Mass) C. Ex. 16 |
|---|---|---|
| cis-3-Hexenol | 5 | 5 |
| Citronellol | 100 | 100 |
| Cyclamen Aldehyde | 100 | 100 |
| Damascenone | 0.5 | 0.5 |
| Ethyl Linalyl Acetate | 50 | 50 |
| Eugenol | 15 | 15 |
| Floralozone[1] | 20 | 20 |
| Helional[2] | 25 | 25 |
| Isodamascone | 1 | 1 |
| MDJ[3] | 200 | 200 |
| Methyl Isoeugenol | 10 | 10 |
| Phenylethyl Alcohol | 250 | 250 |
| Tetrahydrolinalool | 150 | 150 |
| Ylang Ylang Oil No. 1 | 10 | 10 |
| 4-Cyclohexylpentanenitrile (I-3) | 15 | 0 |
| Dipropylene Glycol | 48.5 | 63.5 |
| Total | 1000 | 1000 |

[1]Trade Name of IFF, p-Ethyl-2,2-dimethyl-hydrocinnamicaldehyde
[2]Trade Name of IFF, 2-Methyl-3-(3,4-methylenedioxyphenyl)-propanal
[3]Trade Name of Kao, Methyl dihydrojasmonate The evaluations of the floral (muguet) tone fragrance compositions of Example 24 and Comparative Example 16 were performed in the same manner as in the aforementioned odor evaluation. As compared to the floral (muguet) tone fragrance composition of Comparative Example 16, in the floral (muguet) tone fragrance composition of Example 24, the freshness of a muguet feeling is enhanced, resulting in a fresher fragrance. In the floral (muguet) tone fragrance composition of Example 24, at the same time, expansiveness of the whole fragrance is increased, resulting in a further muguet-like fragrance. In the floral (muguet) tone fragrance composition of Example 24, the 4-cyclohexylpentanenitrile (I-3) substantially emphasized the component forming the muguet tone.

Example 25 and Comparative Example 17

Liquid Softener

The floral (muguet) tone fragrance compositions obtained in Example 24 and Comparative Example 16 each were added to a non-fragranced liquid softener having a composition indicated in Table 15 in such a manner as to be contained in an amount of 0.5% by mass, and thereby liquid softeners of Example 25 and Comparative Example 17 were prepared, respectively.

TABLE 15

| Non-Fragranced Liquid Softener | Blended Amount (% by mass) |
|---|---|
| Quaternary Cationic Softener Base[1] | 5.6 |
| 40% Formaldehyde | 0.1 |
| Ion Exchanged Water | Remainder |
| pH | 3.5 |

[1]Trade Name of Kao: Tetranyl L1/90S

The evaluations of the liquid softeners of Example 25 and Comparative Example 17 were performed as follows. One expert who had an experience of at least five years but less than ten years as well as two experts who had an experience of at least 25 years of blending odors and evaluating fragrances determined the fragrance note of the odor at the mouth of the bottle.

As compared to the liquid softener of Comparative Example 17, in the liquid softener of the Example 25, the freshness of a muguet feeling is enhanced, resulting in a fresher fragrance. In the liquid softener of Example 25, at the same time, expansiveness of the whole fragrance is increased, resulting in a further muguet-like fragrance. In the liquid softener of Example 25, the 4-cyclohexylpentanenitrile (I-3) substantially emphasized the component forming the muguet tone.

Example 26 and Comparative Example 18

Citrus (Bergamot, Lemon) Tone Fragrance Composition

Using the 4-cyclohexylpentanenitrile (I-3) obtained in Example 3, a citrus (bergamot, lemon) tone fragrance composition was prepared in such a manner as to have a composition indicated in Table 16 (Example 26). Furthermore, for comparison, a citrus (bergamot, lemon) tone fragrance composition was prepared without using the 4-cyclohexylpentanenitrile (I-3) (Comparative Example 18).

TABLE 16

| Citrus (Bergamot, Lemon) Tone Fragrance Composition | Ex. 26 | (Unit: Part by Mass) C. Ex. 18 |
|---|---|---|
| Camphor | 20 | 20 |
| Galbanum Oil | 1 | 1 |
| Hexyl Cinnamic Aldehyde[1] | 150 | 150 |
| Iso E Super[2] | 50 | 50 |
| Lemon Oil, California | 50 | 50 |
| Lime Oil | 30 | 30 |

TABLE 16-continued

| Citrus (Bergamot, Lemon) Tone Fragrance Composition | Ex. 26 | C. Ex. 18 |
|---|---|---|
| | | (Unit: Part by Mass) |
| Linalool | 50 | 50 |
| MDJ[3] | 150 | 150 |
| Methylnaphthylketone | 30 | 30 |
| Nerolin Bromelia[4] | 50 | 50 |
| Patchouli Oil | 3 | 3 |
| Petitgrain Oil, Paraguay | 10 | 10 |
| p-tert-Butylcyclohexyl Acetate | 150 | 150 |
| Rosemary Oil | 10 | 10 |
| Terpinyl Acetate | 50 | 50 |
| 4-Cyclohexylpentanenitrile (I-3) | 5 | 0 |
| Dipropylene Glycol | 191 | 196 |
| Total | 1000 | 1000 |

[1] Trade Name of Kao, 2-n-Hexyl-3-phenyl-2-propenal
[2] Trade Name of IFF, 1-(1,2,3,4,5,6,7,8-Octahydro-2,3,8,8-tetramethyl-2-naphthalenyl)-ethan-1-one
[3] Trade Name of Kao, Methyl dihydrojasmonate
[4] Trade Name of Symrise, β-Naphthol ethyl ether The evaluations of the citrus (bergamot, lemon) tone fragrance compositions of Example 26 and Comparative Example 18 were performed in the same manner as in the aforementioned odor evaluation. As compared to the citrus (bergamot, lemon) tone fragrance composition of Comparative Example 18, in the citrus (bergamot, lemon) tone fragrance composition of Example 26, lime-like and galbanum-like odors are enhanced, resulting in not only an improvement in a petitgrain feeling but also a fresh fragrance. In the citrus (bergamot, lemon) tone fragrance composition of Example 26, the diffusibility and intensity of the fragrance also are increased. As compared to the citrus (bergamot, lemon) tone fragrance composition of Comparative Example 18, in the citrus (bergamot, lemon) tone fragrance composition of Example 26, an undesirable chemical odor is concealed very well and thereby a desirable citrus tone is enhanced. In the citrus (bergamot, lemon) tone fragrance composition of Example 26, the 4-cyclohexylpentanenitrile (I-3) substantially emphasized the component forming the citrus tone.

Example 27 and Comparative Example 19

Concentrated Liquid Softener

The citrus (bergamot, lemon) tone fragrance compositions obtained in Example 26 and Comparative Example 18 each were added to a non-fragranced concentrated liquid softener having a composition indicated in Table 17 in such a manner as to be contained in an amount of 1.0% by mass, and thereby concentrated liquid softeners of Example 27 and Comparative Example 19 were prepared, respectively.

TABLE 17

| Non-Fragranced Concentrated Liquid Softener | Blended Amount (% by mass) |
|---|---|
| Quaternary Cationic Softener Base[1] | 16.6 |
| 20% Magnesium Chloride Hexahydrate | 0.2 |
| Preservative[2] | 0.1 |
| Ion Exchanged Water | Remainder |
| pH | 3.5 |

[1] Trade Name of Kao: Tetranyl L1/90S
[2] Trade Name of Lonza: Lonzaserve SG

The evaluations of the concentrated liquid softeners of Example 27 and Comparative Example 19 were performed as follows. One expert who had an experience of at least five years but less than ten years as well as two experts who had an experience of at least 25 years of blending odors and evaluating fragrances determined the fragrance note of the odor at the mouth of the bottle.

As compared to the concentrated liquid softener of Comparative Example 19, in the concentrated liquid softener of Example 27, lime-like and galbanum-like odors are enhanced, resulting in not only an improvement in a petitgrain feeling but also a fresh fragrance. In the concentrated liquid softener of Example 27, the diffusibility and intensity of the fragrance also are increased. As compared to the fragrance composition of Comparative Example 19, in the concentrated liquid softener of Example 27, an undesirable chemical odor is concealed very well and thereby a desirable citrus tone is enhanced. In the concentrated liquid softener of Example 27, the 4-cyclohexylpentanenitrile (I-3) substantially emphasized the component forming the citrus tone.

Example 28 and Comparative Example 20

Woody-Amber Tone Fragrance Composition

Using the 4-cyclohexylpentanenitrile (I-3) obtained in Example 3, a woody-amber tone fragrance composition was prepared in such a manner as to have a composition indicated in Table 18 (Example 28). Furthermore, for comparison, a woody-amber tone fragrance composition was prepared without using the 4-cyclohexylpentanenitrile (I-3) (Comparative Example 20).

TABLE 18

| Woody-Amber Tone Fragrance Composition | Ex. 28 | C. Ex. 20 |
|---|---|---|
| | (Unit: Part by Mass) | |
| Amber Core[1] | 250 | 250 |
| Ambrotech[2] | 50 | 50 |
| Olibanum Resin 50% Dipropylene Glycol Solution | 15 | 15 |
| Patchouli Oil | 10 | 10 |
| Sandalmysore Core[3] | 100 | 100 |
| 4-Cyclohexylpentanenitrile (I-3) | 10 | 0 |
| Dipropylene Glycol | 565 | 575 |
| Total | 1000 | 1000 |

[1] Trade Name of Kao, 1-(2-tert-Butyl cyclohexyloxy)-2-butanol
[2] Trade Name of Kao, Dodecahydro-3a,6,6,9a-tetramethylnaphtho[2,1-b]furan
[3] Trade Name of Kao, 2-Methyl-4-(2,2,3-trimethyl-3-cyclopenten-1-yl)-2-buten-1-ol The evaluations of the woody-amber tone fragrance compositions of Example 28 and Comparative Example 20 were performed in the same manner as in the aforementioned odor evaluation. As compared to the woody-amber tone fragrance composition of Comparative Example 20, the woody-amber tone fragrance composition of Example 28 was provided with sandalwood tone and patchouli tone odors and had an enhanced woody feeling and also an improved long-lasting property. Even after 24 hours, the woody-amber tone fragrance composition of Example 28 was very fresh. In the woody-amber tone fragrance composition of Example 28, the 4-cyclohexylpentanenitrile (I-3) emphasized the component forming the woody tone.

Example 29 and Comparative Example 21

Perfume

The woody-amber tone fragrance compositions obtained in Example 28 and Comparative Example 20 each was added to ethanol in such a manner as to be contained in an amount of 10% by mass, and thereby perfumes of Example 29 and Comparative Example 21 were prepared, respectively.

The evaluations of the perfumes of Example 29 and Comparative Example 21 were performed as follows. Two experts who had an experience of at least five years but less than ten years as well as two experts who had an experience of at least 25 years of blending odors and evaluating fragrances determined the fragrance note by the smelling strip method. About 5 mm of the end of each smelling strip (fragrance test paper with a width of 6 mm and a length of 150 mm) was immersed in a sample and thereby evaluation was performed.

As compared to the perfume of Comparative Example 21, the perfume of Example 29 was provided with sandalwood tone and patchouli tone odors and had an enhanced woody feeling and also an improved long-lasting property. Even after 24 hours, the perfume of Example 29 was very fresh. In the perfume of Example 29, the 4-cyclohexylpentanenitrile (I-3) emphasized the component forming the woody tone.

INDUSTRIAL APPLICABILITY

Since the nitrile compound of the present invention has a spicy tone that is useful as a fragrance, particularly a cumin-like odor, it can be used as a fragrance material. Furthermore, it is stable in an aqueous vehicle. Moreover, the nitrile compound of the present invention can emphasize spicy-, green-, floral-, woody-, and citrus-like odors by being blended with other fragrances. Furthermore, it can suppress oil-, chemical-, and metallic-like undesirable odors. Thus, a fragrance composition containing the nitrile compound of the present invention can be used as a fragrance component for cosmetics, cleaner compositions, softener compositions, etc.

The invention claimed is:

1. A nitrile compound represented by Formula (I-3), Formula (I-2) or Formula (I-1),

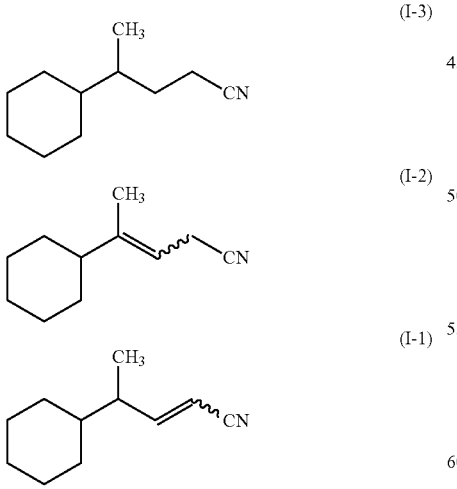

wherein the bond represented by a wavy line in Formula (I-1) and Formula (I-2) indicates a cis form, a trans form, or a mixture of a cis form and a trans form.

2. A nitrile compound according to claim 1, wherein 4-cyclohexyl-2-pentenenitrile represented by Formula (I-1) is obtained by a method comprising condensing 2-cyclohexylpropanal represented by Formula (II) and a cyanomethyl phosphonic acid derivative represented by Formula (III-A) or (III-B),

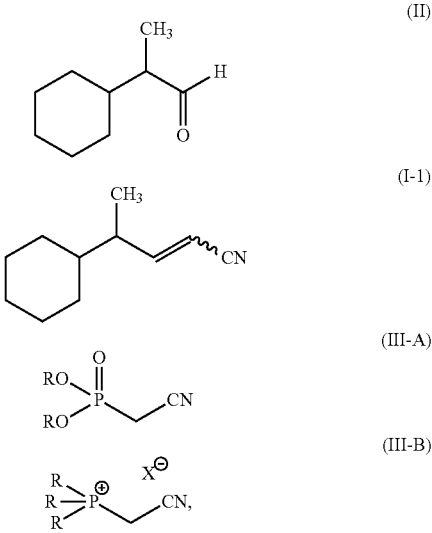

wherein the bond represented by a wavy line in Formula (I-1) indicates a cis form, a trans form, or a mixture of a cis form and a trans form, and R represents an alkyl group having 1 to 6 carbon atoms or a phenyl group and X represents a halogen atom.

3. A nitrile compound according to claim 1, wherein 4-cyclohexyl-3-pentenenitrile represented by Formula (I-2) is obtained by a method comprising condensing 2-cyclohexylpropanal represented by Formula (II) and cyanoacetic acid represented by Formula (IV) and decarboxylating the condensate thus obtained,

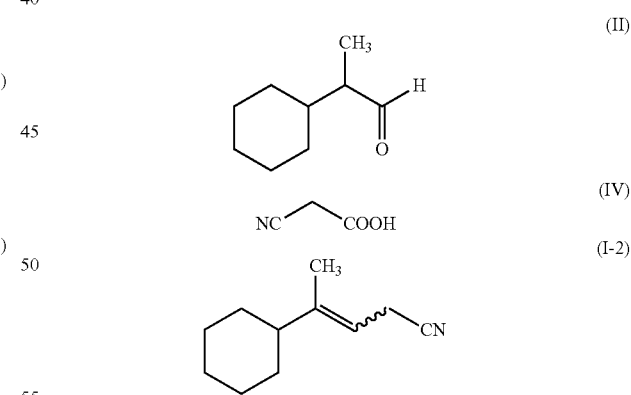

wherein the bond represented by a wavy line in Formula (I-2) indicates a cis form, a trans form, or a mixture of a cis form and a trans form.

4. A nitrile compound according to claim 1, wherein the 4-cyclohexylpentanenitrile represented by Formula (I-3) is obtained by hydrogenating any one member selected from the group consisting of 4-cyclohexyl-2-pentenenitrile represented by Formula (I-1), 4-cyclohexyl-3-pentenenitrile represented by Formula (I-2), and a mixture of 4-cyclohexyl-2-pentenenitrile represented by Formula (I-1) and 4-cyclohexyl-3-pentenenitrile represented by Formula (I-2),

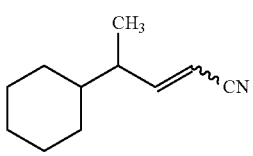

(I-1)

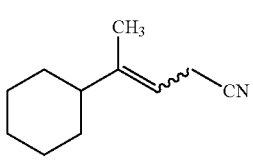

(I-2)

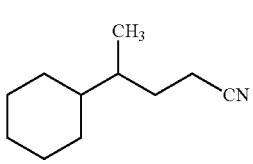

(I-3)

wherein the bond represented by a wavy line in Formula (I-1) and Formula (I-2) indicates a cis form, a trans form, or a mixture of a cis form and a trans form.

5. A fragrance composition comprising a nitrile compound according to claim 1.

6. The fragrance composition according to claim 5, further comprising at least one member selected from the group consisting of a fragrance having a spicy-like odor, a green-like odor, a floral-like odor, a woody-like odor, and a citrus-like odor.

7. The fragrance composition according to claim 5, further comprising a fragrance in addition to the nitrile compound,
wherein the fragrance present in addition to the nitrile compound comprises at least one member selected from the group consisting of a hydrocarbon, an alcohol, a phenol, an aldehyde, a ketone, an acetal, an ether, an ester, a carbonate, a lactone, an oxime, a nitrile, a Schiff base, a natural essential oil, and a natural extract.

8. A fragrance composition comprising a nitrile compound, wherein the nitrile compound is a mixture of 4-cyclohexyl-2-pentenenitrile represented by Formula (I-1) and 4-cyclohexyl-3-pentenenitrile represented by Formula (I-2),

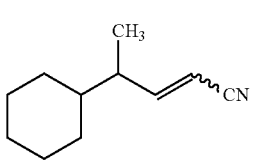

(I-1)

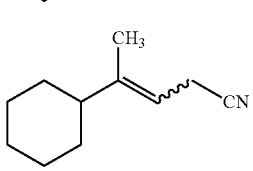

(I-2)

wherein the bond represented by a wavy line in Formula (I-1) and Formula (I-2) indicates a cis form, a trans form, or a mixture of a cis form and a trans form.

9. A fragrance composition according to claim 8, wherein the mixture of 4-cyclohexyl-2-pentenenitrile represented by Formula (I-1) and 4-cyclohexyl-3-pentenenitrile represented by Formula (I-2) is obtained by condensing 2-cyclohexyl-propanal represented by Formula (II) and acetonitrile represented by Formula (V),

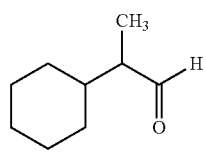

(II)

CH₃CN (V)

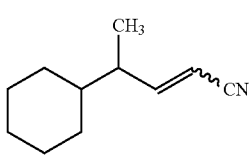

(I-1)

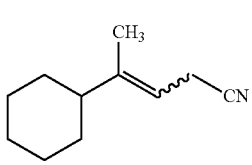

(I-2)

wherein the bond represented by a wavy line in Formula (I-1) and Formula (I-2) indicates a cis form, a trans form, or a mixture of a cis form and a trans form.

10. A fragrance composition according to claim 8, wherein the mixture of 4-cyclohexyl-2-pentenenitrile represented by Formula (I-1) and 4-cyclohexyl-3-pentenenitrile represented by Formula (I-2) is obtained by isomerizing 4-cyclohexyl-3-pentenenitrile represented by Formula (I-2),

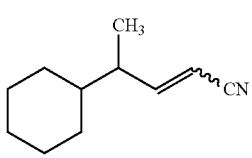

(I-1)

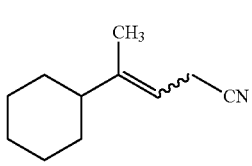

(I-2)

wherein the bond represented by a wavy line in Formula (I-1) and Formula (I-2) indicates a cis form, a trans form, or a mixture of a cis form and a trans form.

11. The fragrance composition according to claim 8, further comprising at least one member selected from the group consisting of a fragrance having a spicy-like odor, a green-like odor, a floral-like odor, a woody-like odor, and a citrus-like odor.

12. The fragrance composition according to claim 8, further comprising a fragrance in addition to the nitrile compound,
wherein the fragrance present in addition to the nitrile compound comprises at least one member selected from the group consisting of a hydrocarbon, an alcohol, a phenol, an aldehyde, a ketone, an acetal, an ether, an ester, a carbonate, a lactone, an oxime, a nitrile, a Schiff base, a natural essential oil, and a natural extract.

13. A method of using a nitrile compound according to claim 1 as a fragrance component for a fragrance composition, a cleaner composition, a softener composition, or a cosmetic, the method comprising adding the fragrance component to the fragrance composition, a cleaner composition, a softener composition, or a cosmetic.

14. A method for using a composition according to claim 5 as a fragrance component for a cleaner composition, the method comprising adding the fragrance component to the cleaner composition.

15. A method for using a composition according to claim 5 as a fragrance component for a softener composition, the method comprising adding the fragrance component to the softener composition.

16. A method for using a composition according to claim 5 as a fragrance component for a cosmetic, the method comprising adding the fragrance component to the cosmetic.

17. A method for using a composition according to claim 8 as a fragrance component for a cleaner composition, the method comprising adding the fragrance component to the cleaner composition.

18. A method for using a composition according to claim 8 as a fragrance component for a softener composition, the method comprising adding the fragrance component to the softener composition.

19. A method for using a composition according to claim 8 as a fragrance component for a cosmetic, the method comprising adding the fragrance component to the cosmetic.

\* \* \* \* \*